US009681919B2

(12) United States Patent
Glossop

(10) Patent No.: US 9,681,919 B2
(45) Date of Patent: Jun. 20, 2017

(54) SYSTEMS, METHODS, AND DEVICES FOR ASSISTING OR PERFORMING GUIDED INTERVENTIONAL PROCEDURES USING CUSTOM TEMPLATES

(71) Applicant: Neil Glossop, Toronto (CA)

(72) Inventor: Neil Glossop, Toronto (CA)

( * ) Notice: Subject to any disclaimer, the term of this patent is extended or adjusted under 35 U.S.C. 154(b) by 95 days.

(21) Appl. No.: 14/795,247

(22) Filed: Jul. 9, 2015

(65) Prior Publication Data
US 2016/0008074 A1    Jan. 14, 2016

Related U.S. Application Data

(60) Provisional application No. 62/022,203, filed on Jul. 9, 2014.

(51) Int. Cl.
*A61B 19/00*    (2006.01)
*A61B 17/02*    (2006.01)
(Continued)

(52) U.S. Cl.
CPC .......... *A61B 19/20* (2013.01); *A61B 17/0218* (2013.01); *A61B 34/10* (2016.02); *A61B 34/20* (2016.02); *A61B 90/10* (2016.02); *A61B 90/11* (2016.02); *A61B 90/39* (2016.02); *A61B 2017/00274* (2013.01); *A61B 2017/00331* (2013.01); *A61B 2017/347* (2013.01); *A61B 2017/3411* (2013.01);
(Continued)

(58) Field of Classification Search
CPC ......... A61B 34/20; A61B 34/10; A61B 90/10; A61B 90/11; A61B 90/39; A61B 17/0218
See application file for complete search history.

(56) References Cited

U.S. PATENT DOCUMENTS

| 4,998,912 A | 3/1991 | Scarbrough |
|---|---|---|
| 6,398,711 B1 | 6/2002 | Green |

(Continued)

FOREIGN PATENT DOCUMENTS

| WO | 2015013716 | 1/2015 |
|---|---|---|
| WO | 2016007717 | 1/2016 |

OTHER PUBLICATIONS

Garg, Animesh, et al., "Robot-Guided Open-Loop Insertion of Skew-Line Needle Arrangements for High Dose Rate Brachytherapy", IEEE Transactions on Automation Science and Engineering, vol. 10, No. 4, Oct. 2013, pp. 948-956.

(Continued)

*Primary Examiner* — Robert N Wieland
(74) *Attorney, Agent, or Firm* — Sheppard Mullin Richter & Hampton LLP

(57) ABSTRACT

Systems, methods, and devices are provided for assisting or performing guided interventional procedures using custom templates. The system uses pre-procedure scans of a patient's anatomy to identify targets and critical structures. A template is then manufactured containing guide elements. During a procedure, the template may be aligned to the patient and instruments passed though the guide elements and into various targets. The template may be aligned using one or more of, for example, a position sensing system or a live imaging modality to register the patient to the template. The system makes optional use of devices designed to immobilize or track an organ during therapy.

47 Claims, 18 Drawing Sheets

(51) Int. Cl.
  *A61B 90/10*   (2016.01)
  *A61B 34/20*   (2016.01)
  *A61B 90/11*   (2016.01)
  *A61B 34/10*   (2016.01)
  *A61B 17/00*   (2006.01)
  *A61B 90/00*   (2016.01)
  *A61B 17/34*   (2006.01)

(52) U.S. Cl.
  CPC .............. *A61B 2034/107* (2016.02); *A61B 2034/2051* (2016.02); *A61B 2090/101* (2016.02); *A61B 2090/363* (2016.02); *A61B 2090/3958* (2016.02)

(56) References Cited

U.S. PATENT DOCUMENTS

| | | | |
|---|---|---|---|
| D466,609 S | 12/2002 | Glossop | |
| 6,785,571 B2 | 8/2004 | Glossop | |
| 7,751,868 B2 | 7/2010 | Glossop | |
| 7,840,251 B2 | 11/2010 | Glossop | |
| 7,840,254 B2 | 11/2010 | Glossop | |
| 8,046,052 B2 | 10/2011 | Verard et al. | |
| 8,073,529 B2 | 12/2011 | Cermak et al. | |
| 8,948,845 B2 | 2/2015 | Glossop et al. | |
| 8,956,364 B2 | 2/2015 | Catanzarite et al. | |
| 2004/0220444 A1 | 11/2004 | Hogendijk | |
| 2004/0259051 A1* | 12/2004 | Brajnovic | A61B 17/176 433/75 |
| 2005/0261707 A1* | 11/2005 | Schatzberger | A61B 8/0841 606/130 |
| 2006/0079867 A1* | 4/2006 | Berzak | A61B 18/02 606/21 |
| 2007/0055128 A1 | 3/2007 | Glossop | |
| 2008/0281329 A1* | 11/2008 | Fitz | A61B 5/4528 606/88 |
| 2012/0041446 A1* | 2/2012 | Wong | A61B 17/1703 606/96 |
| 2012/0265497 A1* | 10/2012 | Leehneer | G01B 17/06 703/1 |
| 2013/0317511 A1* | 11/2013 | Bojarski | A61B 17/1764 606/102 |
| 2013/0338477 A1 | 12/2013 | Glossop et al. | |
| 2014/0049629 A1 | 2/2014 | Siewerdsen | |

OTHER PUBLICATIONS

Osian, Adrian D., et al., "Treatment Planning for Permanent and Temporary Percutaneous Implants with Custom Made Templates", International Journal of Radiation Oncology, Biology, Physics, vol. 16, copyright 1989, pp. 219-223.

Poulin, Eric, et al., "Ultrasound in HDR Brachytherapy: Towards Real-Time 3D Ultrasound Planning and Personalized 3D Printing for Breast HDR Brachytherapy Treatment", Radiotherapy and Oncology, vol. 114, 2015, pp. 335-338.

Roy, Ph.D., Jitendra N., "A CT-Based Evaluation Method for Permanent Implants: Application to Prostate", International Journal of Radiation Oncology, Biology, Physics, vol. 26, Nov. 30, copyright 1993, pp. 163-169.

Roy, Ph.D., Jitendra N., et al., "CT-Based Optimized Planning for Transperineal Prostate Implant with Customized Template", International Journal of Radiation Oncology, Biology, and Physics, vol. 21, copyright 1991, pp. 483-489.

Siauw, Timmy, et al., "NPIP: A Skew Line Needle Configuration Optimization System for HDR Brachytherapy", Medical Physics, vol. 39, No. 7, Jul. 2012, pp. 4339-4346.

Wallner, M.D., Kent, et al., "A New Device to Stabilize Templates for Transperineal I-125 Implants", International Journal of Radiation Oncology, Biology, Physics, vol. 20, copyright 1991, pp. 1075-1077.

Wallner, M.D., Kent, et al., "Fluoroscopic Visualization of the Prostatic Urethra to Guide Transperineal Prostate Implantation", International Journal of Radiation Oncology, Biology, Physics, vol. 29, No. 4, copyright 1994, pp. 863-867.

Xu et al., "Real-Time MRI-TRUS Fusion for Guidance of Targeted Prostate Biopsies," *Computer Aided Surgery*, vol. 13, No. 5, Sep. 2008, pp. 255-264.

Pinto et al., "Magnetic Resonance Imaging/Ultrasound Fusion Guided Prostate Biopsy Improves Cancer Detection Following Transrectal Ultrasound Biopsy and Correlates with Multiparametric Magnetic Resonance Imaging," *The Journal of Urology*, vol. 186, Issue 4, Oct. 2011, pp. 1281-1285.

Gee et al., "3D Ultrasound Probe Calibration Without a Position Sensor," CUED/F-INFENG/TR 488, Sep. 2004 (Cambridge University, Department of Engineering, Trumpington Street, Cambridge CB2 1PZ, United Kingdom), 21 pages.

Lindseth et al., "Probe Calibration for Freehand 3-D Ultrasound," *Ultrasound in Med. & Biol.*, vol. 29, No. 11, 2003, pp. 1607-1623.

* cited by examiner

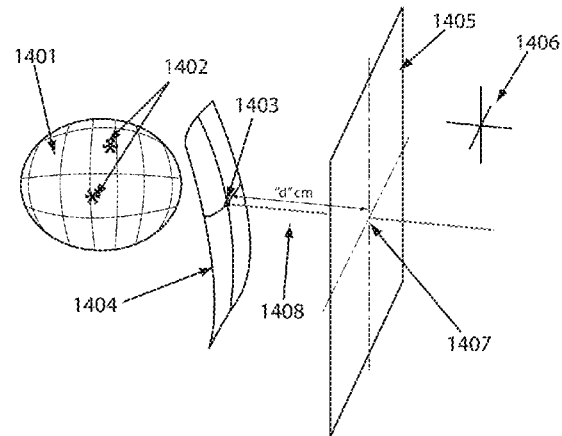
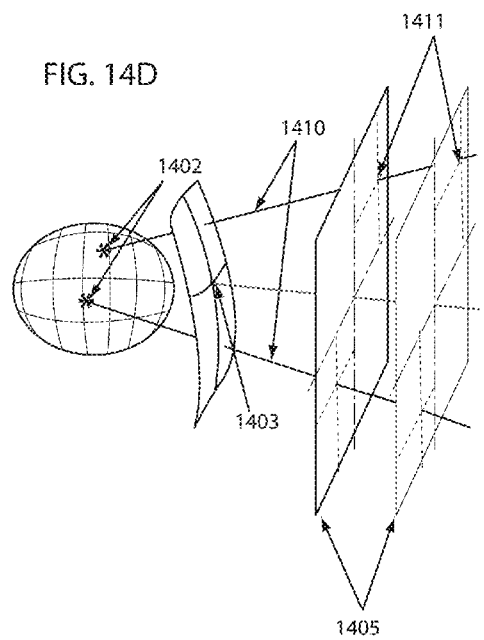
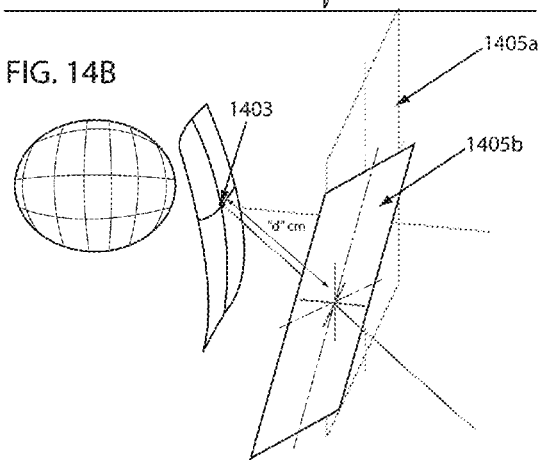
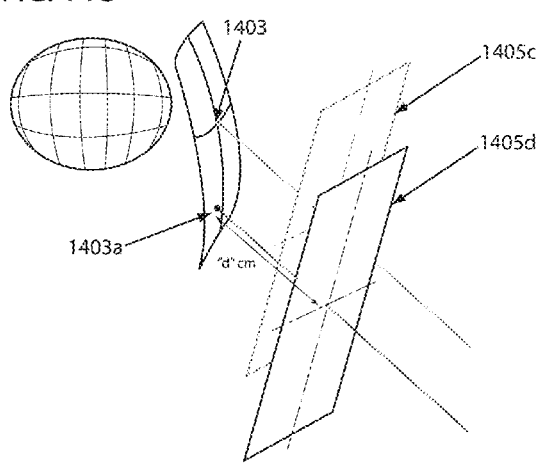

SYSTEMS, METHODS, AND DEVICES FOR ASSISTING OR PERFORMING GUIDED INTERVENTIONAL PROCEDURES USING CUSTOM TEMPLATES

CROSS-REFERENCE TO RELATED APPLICATIONS

This application claims priority to U.S. Provisional Patent Application Ser. No. 62/022,203, filed Jul. 9, 2014, which is hereby incorporated herein by reference in its entirety.

FIELD OF THE INVENTION

The invention relates generally to guided interventional procedures, and more particularly to systems, methods, and devices for assisting or performing guided interventional procedures using custom templates.

BACKGROUND OF THE INVENTION

Many medical procedures rely on imaging for guidance of procedures, particularly those that are minimally invasive such as needle procedures. Needle procedures are routinely performed to deliver drugs, take tissue samples, or perform therapy. Therapies may include, but are not limited to, tissue ablation therapies such as radio frequency ablation, cryoablation, photodynamic therapy, brachytherapy, radiation, laser and microwave ablation; implant of a device such as an artificial heart valve, stent, stent graft, feeding tube, catheter, radioactive seed or electrode; establishment of a channel or pathway such as a shunt; bypass or closure or surgical resection of a portion of tissue; or to place a localization marker or fiducial that can then guide subsequent surgery, radiation therapy etc. to the appropriate location. Many other minimally invasive therapies exist.

When performing these and other minimally invasive interventional procedures, it is important that a physician know the position and orientation of surgical instruments relative to the tissue of interest. While this is sometimes obvious (e.g., direct visualization of an obviously differentiated tissue type), it is often not. Sometimes, diseased tissue may not look different than normal surrounding tissue. Sometimes, an instrument's tip may not be directly visualized and, occasionally, the tissue may not be directly visualized at all. This is especially true for minimally invasive procedures where it is desirable to create as small an entry as possible so structures and tissues of interest may never be visualized.

In many cases, these procedures may be carried out with the assistance of volumetric imaging such as Computed Tomography (CT), Magnetic Resonance Imaging (MRI), or Positron Emission Tomography (PET). They may also be carried out using optical techniques including direct visualization through an endoscope, or through the use of some kind of spectroscopy or fluorescence. Ultrasound imaging (US) and X-ray imaging are also used extensively.

Imaging modalities may also be used before an interventional procedure to plan the treatment or diagnostic procedure, or during the interventional procedure itself to help locate the tissue and/or instruments. X-ray, optical imaging, and US are often regarded as real-time imaging modalities because they may be more portable and convenient than volumetric modalities, and can be easily used during an intervention. In some cases, these imaging devices may not offer as much information as volumetric modalities such as MRI. For example, certain tumors or anatomy that are visible on MRI may not be apparent on US or X-ray, or the quality may be insufficient.

Currently, accurate and easy targeting of a biopsy or therapy device into a target site seen under volumetric methods once a patient has been moved out of the scanner, particularly a CT or MRI scanner, is a challenge since the live device position is not seen on the scans once the scans are complete. The same is true for Cone Beam Computed Tomography (CBCT) and other modalities. While it is possible to perform an intervention in the scanner itself, this may be time consuming, inconvenient, and costly. Ultimately, while many minimally invasive interventions such as needle procedures do have pre-procedure volumetric imaging available, the procedure itself is performed with the assistance of rudimentary imaging devices such as US or X-ray with the pre-procedure volumetric images available only as static films or on a display workstation.

In some cases, such as those performed under X-ray, the anatomy may be visible only during injection of contrast and while the X-ray beam is on. This may expose the surgical team and patient to frequent doses of ionizing radiation and the patient to high doses of nephrotoxic contrast agents. Standard X-rays offer only two dimensional views requiring frequent repositioning of the imager to ensure the instrument is in the correct 3D location in the anatomy.

In some instances, such as those performed using ultrasound (or modifications of US such as Contrast Enhanced Ultrasound (CEUS), or ultrasound elastography), the anatomy may be poorly visualized or presented in a form that makes it difficult for a physician to interpret. Some lesions or anatomy may not be suited to ultrasound at all so it is necessary to "mentally fuse" images from preoperatively-obtained volumetric images with the live ultrasound images.

A physician may also have difficulty identifying a target on the live modality that was previously seen on the pre-operative images especially if they are of different modalities. In some cases, the lesion may be completely invisible under a live modality.

Additionally, it is often desirable to perform a minimally invasive procedure to minimize chances of severe complications that sometimes accompany surgery. By precisely targeting devices, focal cancer lesions treatments, therapy or biopsy locations, it may be possible without subjecting the patient to a large, invasive procedure that would otherwise be poorly tolerated. Only the diseased tissue may be targeted, and healthy tissue spared.

In most cases, the location of an instrument or device must be precisely known in order to properly treat a patient. For example, the location and orientation of a heart valve delivered by a transapical approach must be known prior to deployment. Other examples include placement of biopsy needles prior to sampling, placement of therapy devices as listed above or devices such as implanted fiducials for marking of tumor boundaries for use in later surgery or radiation therapy. In some cases, needles or other instruments may be inserted to monitor therapy. For example, temperature sensors in the form of needles may be inserted to monitor an ablation procedure. When a plurality of devices are implanted such as needles designed to sample multiple locations or ablate multiple portions of a tumor, it is important to accurately place each in a desired location to ensure the therapy is correctly administered.

Currently, needles and other minimally invasive devices may be directed to targets using techniques that may include freehand placement of needles, freehand image-guided needle procedures, needle guides, transperineal saturation guidance, stereotactic frames, robots, or computer assisted image guided intervention.

Needle procedures may be performed freehand and without the use of imaging if the target is large or apparent, such as a large palpable lump or nodule, however image guidance is often preferred. During the technique of freehand needle procedures, needles are typically held in a physician's hand and inserted into the lesion of interest.

Image-guided freehand procedures are similar except that, from time-to-time during the insertion process (or continuously in some cases), an X-ray, CT scan, US, MRI scan, etc. is used to ensure the needle is properly approaching the target and is not impinging on sensitive structures. This is a very common type of needle procedure. For example, during freehand ultrasound-guided needle procedures, an ultrasound transducer may be used to visualize the lesion and path. A needle is then introduced within the scan plane of the transducer so that it can be visualized on its path toward the lesion. This approach may be difficult if the target cannot be easily identified, and may be time consuming or use copious amounts of radiation or contrast agents if X-ray imaging is used.

Another common approach uses "needle guides" that are employed during some ultrasound procedures. In this case, a special guide tube may be attached to an ultrasound transducer. This needle guide is positioned in a known orientation and location relative-to and in the scan plane of the probe, usually by a "click-on" alignment feature. Once attached to the transducer, the paths of a needle placed into the guidance portion of the needle guide can be predicted along the specific path predefined by the guide. The needle path is displayed on the ultrasound screen as a fixed line, and this path is aligned with the lesion and the needle placed into the target for biopsy, treatment, etc. An example of a needle guide may be found in U.S. Pat. No. 8,073,529 to Cermak et al. which is hereby incorporated by reference herein in its entirety.

Prostate biopsy sometimes makes use of a Transrectal Ultrasound (TRUS). A TRUS probe may be positioned in a patient's rectum and a needle guide may be attached to the probe. The tube on the needle guide is used to direct needles into lesions that can be visualized on the ultrasound or, more often, to ensure the needles are sampling within the prostate and not elsewhere.

Needle guides are typically useful in cases where a target is readily visualized by ultrasound, and can restrict the approach (of a physician to the target) to an approach that is in-plane with the viewing plane of the ultrasound. In the prostate, some experts have indicated that transrectal approaches may lead to a greater incidence of infection, and transperineal biopsies may be superior for prostate needle procedures. Needle guides would likely not be useful for Transperineal biopsies.

An alternate approach is a technique known as transperineal saturation biopsy, a template consisting grid of regularly spaced parallel holes placed externally adjacent to the perineum of the patient. A transrectal ultrasound may be introduced and used to observe the sequential placement of needles through the holes in the grid. Needles are inserted into each hole that covers part of the prostate in succession and a sample of the tissue is taken.

Saturation biopsies can be expensive and time-consuming due to the large number of samples (e.g., typically at least sixty, and sometimes twice that number) that are extracted and analyzed. They may also be uncomfortable for the patient.

In some cases, partial or "focal" transperineal biopsies may be performed in which a subset of a saturation biopsy is used to selectively target certain locations within the prostate or tissue being sampled. Based on a scan or other knowledge of the probable location of the cancer (such as the results of a prior biopsy), the suspected area may be preferentially sampled. Even in these reduced biopsies, usually at least 30 biopsy cores are obtained.

Various robotically-assisted biopsy techniques are known, using multi-axis robots that serve as a needle aiming and holding devices. Based on preoperative volumetric scans, a robot is first registered to a patient. The needle held by the robot is then aligned to the target automatically. A physician delivers the needle to the target either by hand pushing the needle or by directing the robot to do so using an electromechanical control mechanism.

Stereotactic biopsy has been used for many years. In this method, a frame is fitted to the patient, typically to the head, in order to obtain needle access to a lesion in the brain. The location of the target relative to the location of the frame is determined from scans, and a needle on the frame is aligned to the target using dials and precise scales to move and angle the needle. It is then inserted in a straight path through a trephination or burr hole into the location in the brain.

Various forms of stereotaxy exist, but the technique is currently mainly limited to radiosurgery or radiotherapy using external radiation beams as stereotactic frames, and needles are rarely used any more. The technique is regarded as complex and fairly invasive, and has been largely replaced by computer assisted "frameless stereotaxy" (described below).

The advent of accurate and inexpensive position sensors has enabled methods of Image-Guided Interventions (IGI) (also known as "frameless stereotaxy") to be used to bring an instrument to the location of a target during an interventional procedure. Proper localization including position and orientation of these devices is critical to obtain the best result and patient outcome.

Some IGI systems use an externally placed locating device (also known as tracking systems or position sensors), such as a camera system or magnetic field generator together with an instrument containing a trackable component or "position indicating element" that can be localized by a locating device or tracking system (collectively referred to hereinafter a "tracking device"). Depending on the device and technology, these use infrared light emitting diodes (LEDs), reflective spheres, or small electromagnetic sensing coils as position indicating elements.

Position indicating elements are associated with a coordinate system and are typically attached to instruments such as surgical probes, drills, microscopes, needles, X-ray machines, etc., and to the patient. The spatial coordinates and often the orientation (depending on the technology used) of the coordinate system associated with the position indicating elements can be determined by the tracking device in the fixed coordinate system (or fixed "frame of reference") of the tracking device. Many tracking devices may be able to track multiple position indicating elements simultaneously in their fixed frame of reference. Through geometrical transformations, it is possible to determine the position and orientation of any position indicating element relative to a frame of reference of any other position indicating element tracked by the same tracking device.

A variety of different tracking devices exist, having different advantages and disadvantages. For example, optical tracking devices may be constructed to enable the highly accurate position and orientation of a tool equipped with position indicating elements to be calculated. An example of an optical tracking device is the Polaris Vicra (Northern Digital Inc., Waterloo, ON Canada). Optical tracking devices suffer from line-of-site constraints, as they rely on triangulation of a light-emitting diode or reflective marker with several cameras.

An example of an Electromagnetic (EM) tracking device is the Aurora (Northern Digital Inc., Waterloo, ON Canada). EM tracking devices do not require a line-of-sight between the tracking device and the position indicating elements. EM tracking devices may be used with flexible instruments where position indicating elements are placed at the tip of the instruments. Other known tracking devices include, but are not limited to, mechanical linkage devices, fiber optic devices, ultrasonic devices and global positioning devices.

Image guided interventions using these systems can be effectively performed if an accurate "registration" is available to mathematically map the position data of position indicating elements expressed in terms of the coordinate system of the tracking device ("patient space") to the coordinate system of the externally imaged data ("image space") determined at the time the images were taken. In rigid objects such as the skull or bones, one method of registration is performed by using a probe equipped with position indicating elements (therefore, the probe itself is tracked by a tracking device) to touch fiducial markers (such as, for example, small steel balls (x-spots) made by the Beekley Corporation, Bristol, Conn.) placed on the patient prior to imaging. This enables the system to obtain the patient space coordinates of the fiducials. These same fiducials are visible on an image such as, for example, a CT scan and are identified in the image space by indicating them, for example, on a computer display. Once these same markers are identified in both spaces, a registration transformation or equivalent mathematical construction can be calculated. In one commonly used form, a registration transformation may comprise a 4×4 matrix that embodies the translations, magnification factors and rotations required to bring the markers (and thus the coordinate systems) in one space in to coincidence with the same markers in the other space.

Fiducial markers used for registration may be applied to objects such as bone screws or stick-on markers that are visible to the selected imaging device, or can be implicit, such as unambiguous parts of the patient anatomy. These anatomical fiducials may include unusually shaped bones, osteophytes or other bony prominence, calcifications, features on blood vessels or other natural lumens (such as bifurcations of bronchial airways), individual sulci of the brain, or other markers that can be unambiguously identified in the image and patient. A rigid affine transformation such as the 4×4 matrix described above may require the identification of at least three pairs of non-collinear points in the image space and the patient space. Often, many more points are used and a best-fit may be used to optimize the registration. It is normally desirable that fiducials remain fixed relative to the anatomy from the time of imaging until the time that registration is complete.

Registration for image-guided surgery may be accomplished using different methods. Paired-point registration (described above) is accomplished by a user identifying points in image space and then obtaining the coordinates of the corresponding points in patient space.

Another type of registration, surface registration, can be done in combination with, or independent of, paired point registration. In surface registration, a cloud of points is obtained in the patient space and matched with a surface model of the same region in image space. A best-fit transformation relating one surface to the other may then be calculated. In another type of registration, repeat-fixation devices may be used that involve a user repeatedly removing and replacing a device in known relation to the patient or image fiducials of the patient.

Automatic registration may also be performed. Automatic registration may, for example, make use of predefined fiducial arrays or "fiducial shapes" that are readily identifiable in image space by a computer. The patient space position and orientation of these arrays may be inferred through the use of a position indicating element fixed to the fiducial array. Other registration methods also exist, including methods that attempt to register non-rigid objects generally through image processing means.

Registrations may also be performed to calculate transformations between separately acquired images. This may performed by identifying "mutual information" (e.g., the same fiducial markers existing in each image set). In this regard, information visible in one image, but not the other, may be coalesced into a combined image containing information from both.

One such method for doing "image-image co-registration" for ultrasound and MRI was presented by Xu et at in "Real-time MRI-TRUS Fusion for Guidance of Targeted Prostate Biopsies," Computer Aided Surg., 2008 September; 13(5): 255-264. Another method of registration of pre-procedure and intra-procedure images is disclosed in U.S. patent application Ser. No. 13/918,413 to Glossop et al., filed Jun. 14, 2013, entitled "System, Method and Device for Prostate Diagnosis and Intervention," each of which is hereby incorporated by reference herein in its entirety. These methods include the co-registration or matching of two sets of similar but non-identical three dimensional images. The images are not identical even when the same modality is used due to the movement of tissue and the patient between the times of the scans. When the modalities differ (e.g., ultrasound and MRI), the images also differ. Co-registration may take the form of rigid, affine, non-rigid (deformable) etc. methods, many of which are well known in the art and are a continuous area of research.

Once the images have been co-registered, a mapping is available that is able to take a point or region on one image set and transfer it to the other image set.

In certain implementations, the location of lesions, targets or regions of interest may be copied or transferred on to other images. For example, if a region or target was detected on MRI, it may be transferred onto CT images, X-ray images, PET images, Ultrasound images, or other MRI images, for example. This may be done, for instance, by using the aforementioned transformation to transform coordinates from the first image space to the second image space. This "combined image space" may in turn be registered to the patient space using the techniques mentioned above.

Following registration, the two or more spaces are linked through the transformation calculations. Spaces that may be linked may include for example patient and image, image and image, or multiple images and patient. Once registered, the position and orientation of a tracked probe placed anywhere in the registered region may be located on, for example, a scan or set of scans of the region. Likewise, it may be possible to point to a location on one scan and have the matching location be displayed on another scan.

When performing an intervention, a tracking device may be used. Typically the tracking device if used may be connected to a computer system. Scans may also be loaded on to the computer system. The computer system display may take the form of a graphical representation of a probe or an instrument's position superimposed on to preoperative image data. Accordingly, it is possible to obtain information about the object being probed as well as the instrument's position and orientation relative to the object that is not immediately visible to the surgeon. The information displayed can also be accurately and quantitatively measured enabling the physician to carry out a preoperative plan more accurately.

In an image-guided intervention, it is desirable to plan the placement of a device or instrument in a precise pre-planned location (e.g., defining both its location in three dimensions (e.g., its x, y, z location) as well as its orientation (roll, pitch, yaw)). Because of the interdependence and coupling of orientation and translation, it is typically extremely difficult and tedious to manually align the instrument with the preplanned location in all 6 degrees of freedom (all translations and rotations) simultaneously even with computer feedback relaying the distance from the planned positions and orientations. As soon as some of the degrees of freedom are aligned, attempts to align subsequent rotations or translations cause the other degrees of freedom to fall out of alignment. While it is usually possible to converge on the correct alignment, it may take some time to do so. It is also not intuitive as to how to move the probe to easily achieve this alignment.

An additional concept in image-guided intervention is that of "dynamic referencing". Dynamic referencing may account for any bulk motion of the anatomy or part thereof relative to a tracking device. This may entail attachment of additional position indicating elements to the anatomy, or other techniques. For example, in cranial surgery, position indicating elements that form the dynamic reference are often attached directly to the head or more typically to a clamp meant to immobilize the head. In prostate surgery, a special Foley catheter may be used to track the prostate with the use of a position indicating element embedded in the catheter (see U.S. Pat. No. 8,948,845 to Glossop et al., entitled "System, Methods, and Instrumentation for Image Guided Prostate Treatment," which is hereby incorporated by reference herein in its entirety). In spine surgery, a dynamic reference attached (via a temporary clamp or screw) to the vertebral body undergoing therapy is used to account for respiratory motion, iatrogenic motion, as well as motion of the tracking device.

"Gating" may also be used to account for motion of the anatomy. Rather than continually compensating for motion through dynamic referencing, "gated measurements" are measurements that are only accepted at particular instants in time. Gating has been used in, for example, cardiac motion studies. Gating synchronizes a measured movement (e.g., heartbeat, respiration, or other motion) to the start of the measurement in order to eliminate the motion. Measurements are only accepted at specific instants. For example, gating during image guided intervention of the spine may mean that the position of a tracked instrument may be sampled briefly only during peak inspiration times of a respiratory cycle.

Both registration and use of an image guided intervention system in the presence of anatomical motion (such as that which occurs during normal respiration) is generally regarded as safer and more accurate if a dynamic reference device is attached prior to registration (and/or if gating is used). Instead of reporting the position and orientation of a position indicating element of a tracked instrument in the fixed coordinate system of the tracking device, the position and orientation of the position indicating element of the tracked instrument is reported relative to the dynamic reference's internal coordinate system. Any motion experienced mutually by both the dynamic reference and the tracked instrument is "cancelled out."

With reference to FIG. 1, an organ 101 is depicted (e.g., a prostate gland, kidney, liver, thyroid, or other organ) containing a suspected tumor 102. Tumor 102 may be have been detected by an imaging modality such as MRI, multiparametric MRI, CT, PET, ultrasound, or by some other method. Once detected, it may be desirable to place a needle into tumor 102 for the purposes of biopsy, therapy, or delivering fiducials, for example.

The article by Pinto et al., entitled "Magnetic Resonance Imaging/Ultrasound Fusion Guided Prostate Biopsy Improves Cancer Detection Following Transrectal Ultrasound Biopsy and Correlates with Multiparametric Magnetic Resonance Imaging," The Journal of Urology, Volume 186, Issue 4, 1281-1285, which is hereby incorporated by reference herein in its entirety, demonstrates the use of multiparametric MRI in the detection of prostate cancer. Once it is visualized on an imaging modality such as MRI, it may be annotated on the MRI scans. It may also, for example, be segmented so that its three dimensional boundaries are visible on the scans. The suspected cancer regions may be marked as single points, as indicated by asterisk (*) point 103. The spatial location, size, and/or orientation may also be modeled or notated and stored in a database or in reference to the images on which it was detected.

In some instances, an organ or region may be segmented or delineated so that its boundaries are apparent. This may assist a physician in understanding the boundaries of the organ. It may further assist in registering the position and orientation of the organ with subsequent images of the organ and, for example, enable it to be projected or fused into images obtained using another imaging modality. For instance, a three-dimensional graphic rendering representing a prostate gland that has been segmented from MRI may be fused with a real-time imaging modality such as ultrasound rather than the actual MRI images. The organ, in addition to critical structures within or around the organ such as important vessels, nerves, ducts, stones, bones, valves, nodes, and other regions of interest may be segmented.

As shown in FIG. 1, a number of needles 104a, 104b, 104c, and 105 are shown converging onto the tumor, specifically suspected cancer region 103. The needles may be positioned for the purposes of sampling tissue (e.g., for a biopsy) or delivering a treatment as mentioned previously. Both the position and orientation of the needles are important so that while needles 104a, 104b, and 104c may be acceptably placed, needle 105 may transect a structure 106 (e.g., such as the urethra) which may not be acceptable. Using the methods explained above, a physician would attempt to avoid this structure. For example, in a transperineal saturation biopsy of the prostate, a physician may use imaging to constantly monitor for a needle that will violate the urethra.

In a prior art depiction shown if FIG. 2, a needle 201 is equipped with an electromagnetic tracking sensor or position indicating element 202 that, when connected to a position sensor 203, enables its location and orientation in space to be detected. Position sensor 203 may determine the location of position indicating element 202 in a frame of reference 204 so that a transformation matrix "[T0]" may be reported that determines a translation and rotation to locate position indicating element 202 (and thus the tip of needle 201) in frame of reference 204. Similar devices have been disclosed previously for example in U.S. Pat. No. 6,785,571 to Glossop, entitled "Device and method for registering a position sensor in an anatomical body," which is hereby incorporated by reference herein in its entirety.

A registration step may be performed to relate the position of the actual anatomy 206 in frame of reference 204 with the images 207 of the anatomy. This transformation is indicated as "[T1]" in FIG. 1. This enables a graphic display 209 of the needle on the pre-procedure images 207, which moves around as the needle 201 is moved. Needle 201 may then be placed into the lesions or suspected lesions 210 by observing the graphic display 209 of the needle while manipulating the actual needle 201. When the graphic display 209 of the needle is shown to be in the correct trajectory, needle 201 may be placed into the anatomy 206 and subsequently into lesion 210. There are numerous ways to perform this registration to obtain T1, some of which are referenced above.

In some implementations, an ultrasound, X-ray, or other live imaging modality may be used in conjunction with the pre-procedure images. In one implementation, an ultrasound transducer 211 may be equipped with a position indicating element 212 that indicates the position and orientation of transducer 211 relative to frame of reference 204, indicated here as transformation "T2." If a calibration has been performed, the location and orientation of the scan plane 214 of transducer 211 is known as a fixed transformation "T3." From this, points in the anatomy 206 on the scan plane 214 together with transformations T1, T2, and T3 can yield the location of these points on pre-procedure images 207, and it is possible to fuse the preoperative images with the live images. If the location of needle 201 is known through transformation T0, it too can be projected on the preoperative and intraoperative images.

Methods of ultrasound calibration to determine T3 are known in the art, some of which are summarized in the document to Gee et al., entitled "3D Ultrasound Probe Calibration Without A Position Sensor," CUED/FINFENG/TR 488, September 2004 (Cambridge University, Department Of Engineering, Trumpington Street, Cambridge CB2 1PZ, United Kingdom), and in the document to Lindseth et al., entitled "Probe Calibration for Freehand 3-D Ultrasound," each of which is hereby incorporated herein by reference in its entirety.

Templates or guides have been used in orthopedic surgery as well as a number of commercial manufacturing procedures that require cutting, drilling or assembly operations. Templates are guides that include guide elements such as holes and slits that are placed in a precise location over a work piece. Tools such as saws or drill are used to create holes or cuts in the work piece by first attaching the template to the work piece, and then placing the tools into the guide elements of the template and performing the cutting or drilling operation. The elements in the template are defined a priori so that if the work piece is properly aligned, the holes and cuts will be in the correct location.

In instances relating to orthopedic surgery, patient-specific templates have been employed. For example, U.S. Pat. No. 8,956,364 to Catanzarite et al., entitled "Patient-Specific Partial Knee Guides and Other Instruments" describes a cutting guide that differs from standard cutting guides used for total knee arthroplasty because it uses a template that is custom machined to the contours of the patient's bone to help align it. It is placed into the best matching position on the bone and, once in place, it may be used to guide the cuts in the bone directly or assist in mounting one or more cutting guides.

Medical templates are used exclusively for hard tissues, such as bone, since they can be aligned against hard immovable features on the bone. Unfortunately, soft tissues are not amenable to alignment using templates in the same way as bone, because templates cannot engage (and therefore be affixed to) soft tissues. These and other drawbacks exist.

SUMMARY OF THE INVENTION

The invention addressing these and other drawbacks in the art relates to systems, methods, and devices for assisting or performing guided interventional procedures using custom templates.

According to an aspect of the invention, pre-procedure scans of a patient's anatomy may be used to identify targets and critical structures. A template is then manufactured containing one or more guide elements. During a procedure, the template may be aligned to the patient, and instruments may be passed though the guide elements, and into various targets. The template may be aligned using one or more of, for example, a position sensing system or a live imaging modality to register the patient to the template. The system makes optional use of devices designed to immobilize or track an organ during therapy.

One advantage of the invention is that the systems, methods, and devices described herein facilitate procedures that require the localization of one or more surgical instruments relative to soft tissue anatomy.

An additional advantage of the invention is that the systems, methods, and devices described herein facilitate procedures that may benefit from the placement of individualized templates to guide interventions or biopsies, particularly where multiples needles or devices must be placed into specific locations within a tissue.

Yet another advantage of the invention is that the templates described herein may increase accuracy and speed an operation such as drilling or cutting. Once a template is in place, multiple operations may be performed at once without the need to realign the template since the template may contain several guiding elements or features.

These and other objects, features, characteristics, and advantages of the systems, methods, and devices disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 14A-14D are exemplary depictions of method steps for positioning a template, and for generating paths through the template, according to an aspect of the invention.

DETAILED DESCRIPTION OF THE INVENTION

Described herein are systems, methods, and devices for assisting or performing guided interventional procedures using custom templates for the purpose of, among other things, marking or annotating regions, providing therapy to a region, sampling an aspect of a region, or cutting or manipulating a region.

Examples of guided interventional procedures may include, but are not limited to, procedures such as surgical resections, biopsies, full or focal ablation of a tumor or tissue, injection of an agent such as a drug, placement of fiducials, placement of brachytherapy seeds, marking or resection of the skin in preparation for a surgical procedure, marking or resection of an aspect of anatomy that is either a target or a critical location that must be avoided, placing monitoring sensors such as temperature sensors, placing stabilizing instruments, placement of devices such as stents or stent grafts, and placement of cardiac valves or other such devices. Guided interventional procedures may also include marking and manipulation of tissues or fragments thereof.

Guided interventional procedures may further make use of therapeutic devices such as, for example, needles, ablation needles, radio frequency ablation needles, lasers and laser delivery systems, blades, cryoablation needles, microwave ablation needles, HIFU delivery systems, and radiation delivery devices, as well as various other therapeutic devices. Such procedures may also make use of monitoring probes for measuring temperature or dose, etc. Such procedures may further make use of probes that perform a protective function such as cooling an area that is adjacent to a region that is being ablated using heat, etc.

Exemplary System Configuration

Figure 3:
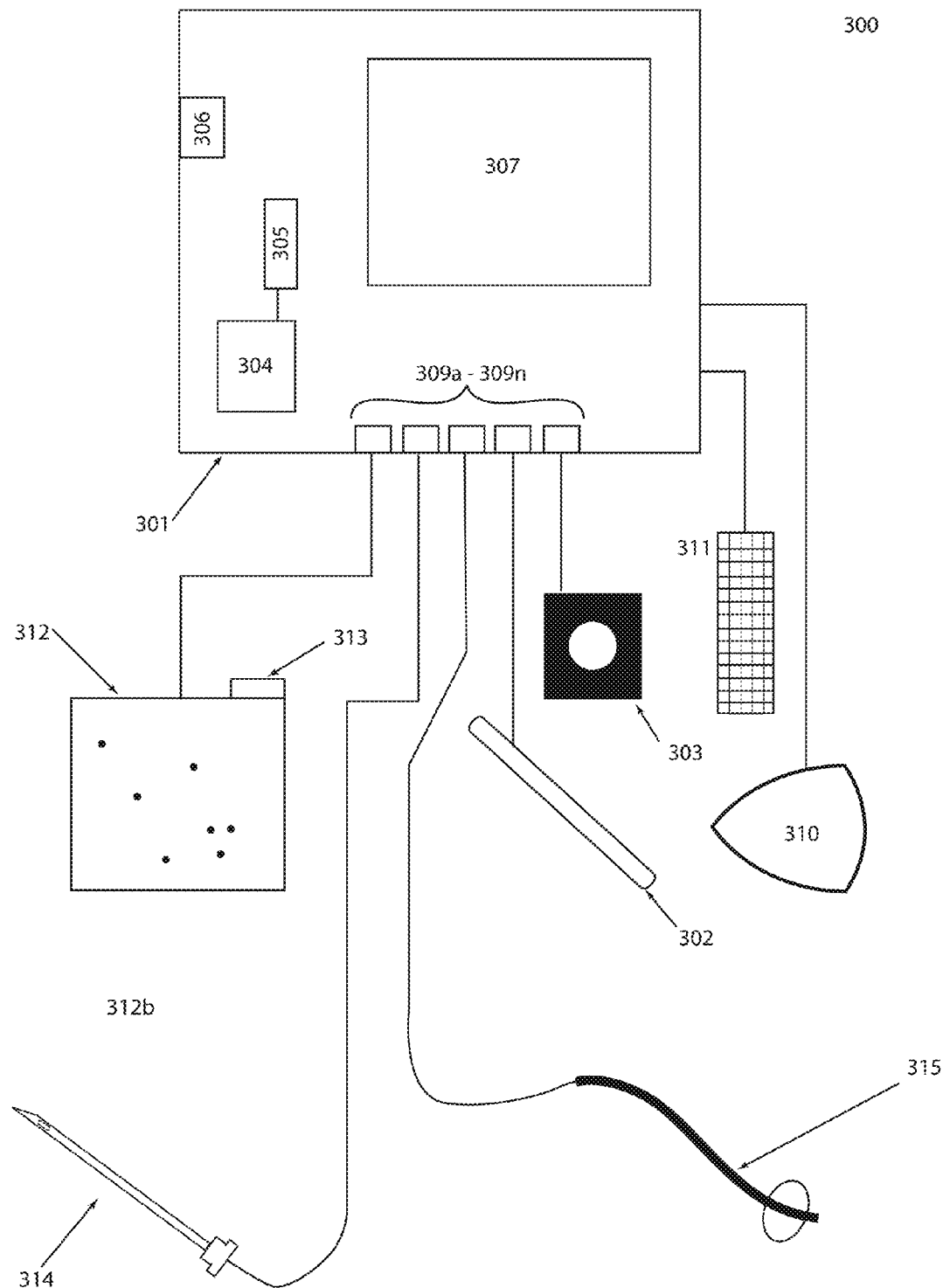
FIG. 3 is a schematic view of an exemplary system for assisting or performing guided interventional procedures using custom templates, according to an aspect of the invention.

FIG. 3 is a schematic view of an exemplary (and non-limiting) system 300 for assisting or performing guided interventional procedures using custom templates, according to an aspect of the invention.

System 300 may include a computer device 301, a tracking device 302, an imaging device 303, a template assembly 312, one or more surgical device or surgical device assemblies 314, a dynamic reference device 315, or other components.

Computer Device 301

Computer device 301 may be or include one or more servers, personal computers, portable (e.g., laptop) computers, mobile computers, tablet computers, cell phones, smart phones, PDAs, or other computer devices. Computer device 301 may send, receive, store, or manipulate data necessary to perform any of the processes, calculations, image formatting, image display, or other processing operations described herein. Computer device 301 may also perform any processes, calculations, or processing operations necessary for the function of the devices, instruments, or other system components described herein.

Computer device 301 may include one or more processor(s) 304, one or more storage device(s) 305, a power source 306, a control application 307 comprising computer program instructions, one or more inputs/outputs 309a-309n, at least one display device 310, one or more user input devices 311, or other components.

Processor(s) 304 may include one or more physical processors that are programmed by computer program instructions that enable various features and functionality described herein. For example, processor(s) 304 may be programmed by control application 307 (described below) and/or other instructions.

Storage device 305 may comprise random access memory (RAM), read only memory (ROM), and/or other memory. The storage device may store the computer program instructions to be executed by processor(s) 304 as well as data that may be manipulated by processor(s) 304. Storage device 305 may also comprise floppy disks, hard disks, optical disks, tapes, or other storage media for storing computer-executable instructions and/or data.

Display device 310 may comprise a computer monitor or other visual display device such as, for example, an LCD display, a plasma screen display, a cathode ray tube display, or other display device.

Input device 311 may comprise a mouse, a stylus, a keyboard, a touchscreen interface (which may be associated or integrated with display device 310), a voice-activated input device (e.g., including a microphone and/or associated voice processing software), or other device that enables a user (e.g., a physician performing a procedure, an assistant thereto, or other user) to provide input to computer device 301 and/or other components of system 300. One or more input devices 311 may be utilized. In one implementation, display device 310 and input device 311 may together be configured as a mobile computing platform such as a tablet computer that is connected wirelessly to computer 301. Other configurations may be implemented.

Inputs/outputs 309a-309n enable various system components such as tracking device 302, imaging device 303, template assembly 312, one or more surgical device or surgical device assemblies 314, dynamic reference device 315, or other components to communicate with computer device 301 (e.g., in a wired or wireless manner) as known and understood by those having skill in the art.

Although not illustrated in FIG. 3, computer device 301 may be connected to other computer devices and/or other system components via a network, which may include any one or more of, for instance, the Internet, an intranet, a PAN (Personal Area Network), a LAN (Local Area Network), a WAN (Wide Area Network), a SAN (Storage Area Network), a MAN (Metropolitan Area Network), a wireless network, a cellular communications network, a Public Switched Telephone Network, and/or other network.

Computer device 301 may further be operatively connected (e.g., via the aforementioned network) to one or more databases. A database may be, include, or interface to, for example, an Oracle™ relational database sold commercially by Oracle Corporation. Other databases, such as Informix™, DB2 (Database 2) or other data storage, including file-based, or query formats, platforms, or resources such as OLAP (On Line Analytical Processing), SQL (Structured Query Language), a SAN (storage area network), Microsoft Access™ or others may also be used, incorporated, or accessed. The database may comprise one or more such databases that reside in one or more physical devices and in one or more physical locations. The database may store a plurality of types of data and/or files and associated data or file descriptions, administrative information, or any other data, as described herein.

Tracking Device 302

In some implementations, tracking device 302 may be used. Tracking device 302 may comprise, for example, an electromagnetic tracker, an optical tracker, a GPS tracker, an acoustic tracker, a mechanical tracking system, or other tracking device.

Imaging Device 303

Imaging device 303 may include X-ray equipment, computerized tomography equipment, positron emission tomography equipment, magnetic resonance imaging equipment, fluoroscopy equipment, ultrasound equipment, an isocentric fluoroscopic device, a rotational fluoroscopic reconstruction system, a multi-slice computerized tomography device, an intravascular ultrasound imager, an optical coherence tomography (OCT) device, an optical imaging device, a single photon emission computed tomography device, a magnetic particle imaging device, or other imaging/scanning equipment.

Figure 1:
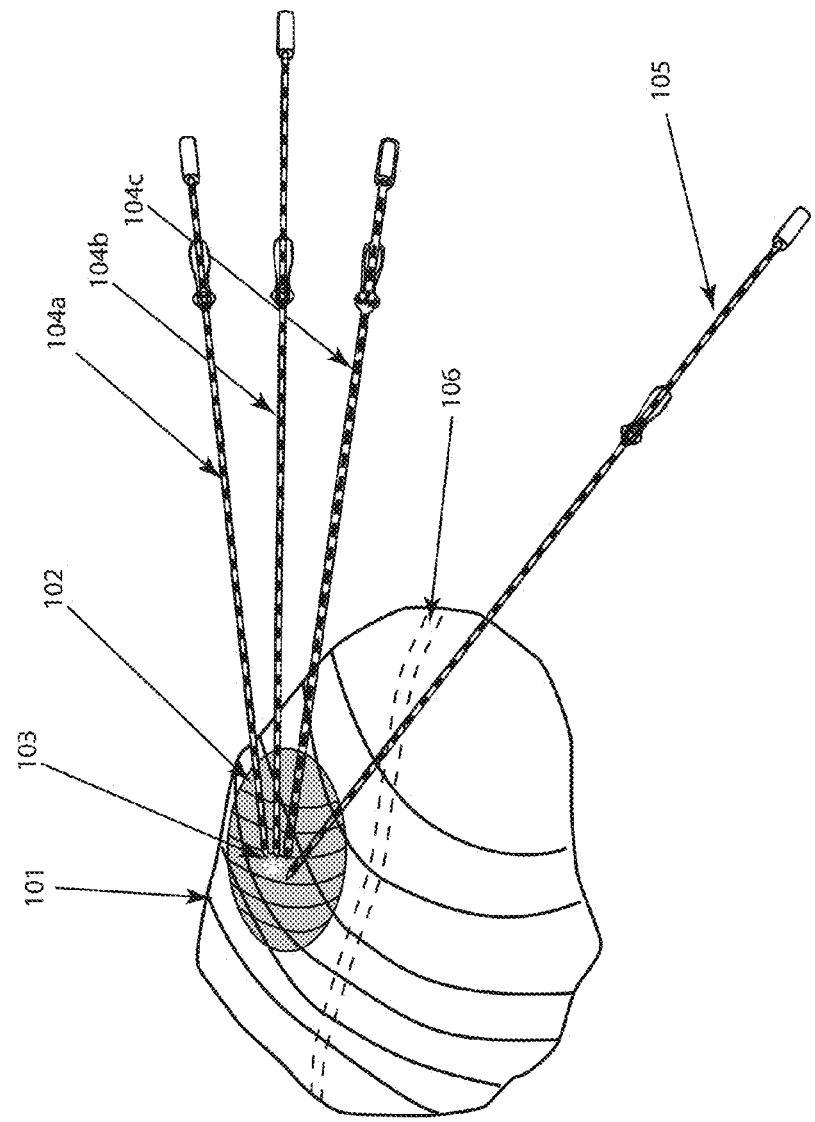
FIG. 1 depicts needles targeted toward a suspected lesion in an organ, including a needle that traverses a sensitive structure.
Figure 2:
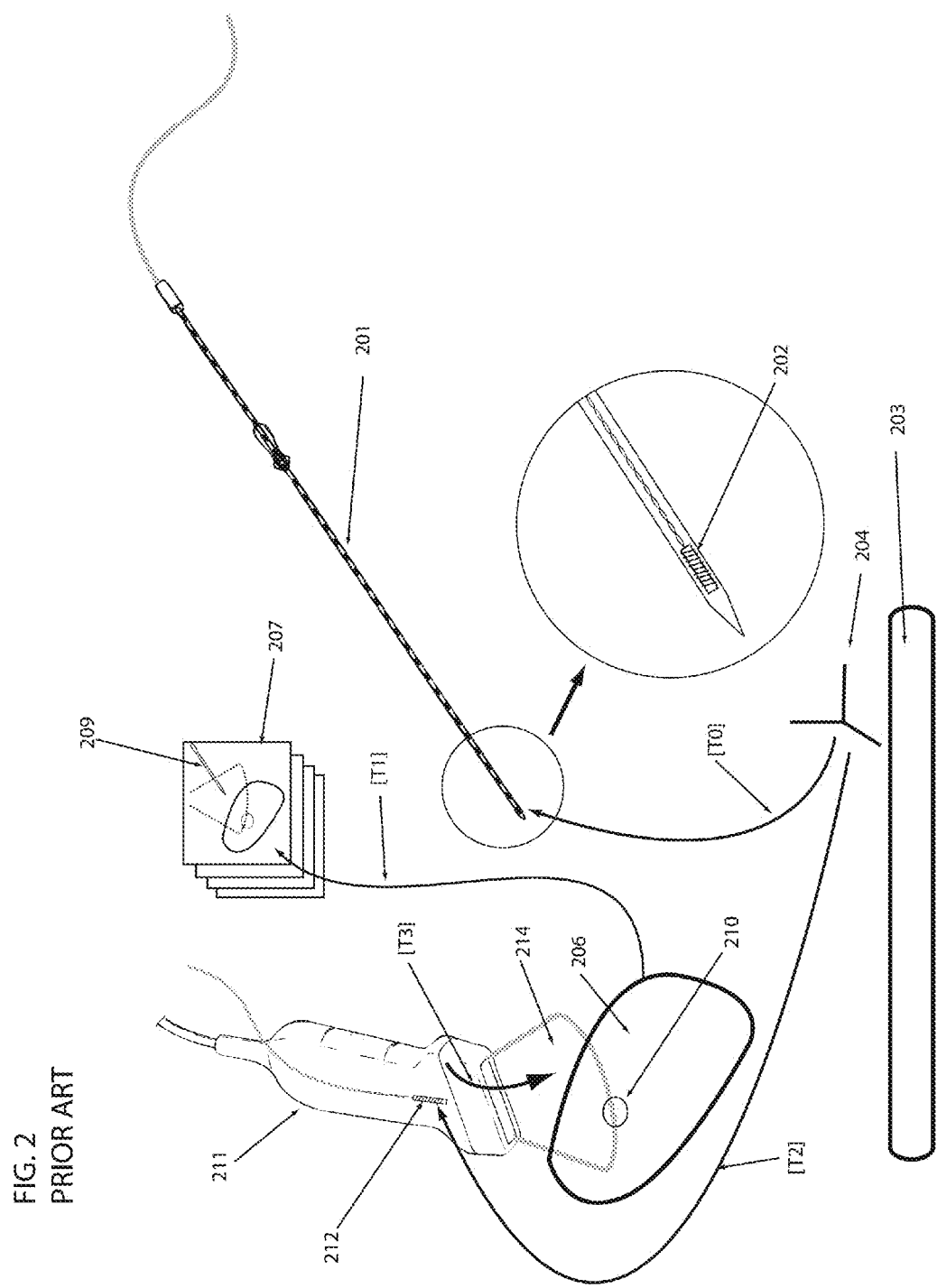
FIG. 2 illustrates a prior art system in which an ultrasound equipped with position indicating elements is used together with a needle containing a position indicating element to place a needle in a patient's anatomy.

In some implementations, imaging device 303 may include one or more devices so that its location and orientation may be tracked by tracking device 302. For example, an ultrasound device may include a position-indicating element enabling its scan plane to be known as shown in FIG. 2. Similarly, a fluoroscope may include a tracking target such as that described in U.S. Pat. No. 8,046,052 to Verard et al., and illustrated in U.S. Design Pat. No. D466,609 to Glossop, each of which is hereby incorporated herein by reference in its entirety.

Template Assembly 312

According to an aspect of the invention, template assembly 312 may comprise a template (also referred to as a targeting template or guide) and a position-indicating element or template tracker 313, which may be attached (permanently or removably) to the template or to a frame that surrounds (or encompasses) all or a portion of the template. Templates are described in greater detail herein.

Template tracker 313 may comprise a mechanical encoder, or an optical, electromagnetic, or other tracker (described in greater detail below) that can be tracked by tracking device 302.

Further, although not illustrated in FIG. 3, the template assembly may further comprise a support mechanism or structure used to support and/or position the template assembly vis-à-vis a target (e.g., a patient's anatomy). The support mechanism may comprise dials or other controls to adjust and fine tune the position of the template. Examples of a support mechanism may include a Biojet (D&K Technologies GmbH, Barum Germany) or the Multi-purpose Workstation LP (Civco Inc., Coralville Iowa) that may include motors and/or encoders. In one implementation, the template assembly may be supported and/or moved into position in an automated manner using a robotic mechanism attached to the support mechanism.

Surgical Devices or Device Assemblies 314

In some implementations, system 300 may include one or more surgical devices or device assemblies 314, the position and orientation of which may be tracked by tracking device 302. Examples of surgical devices may include therapeutic devices such as needles, ablation needles, radio frequency ablation needles, lasers and laser delivery systems, blades, cryoablation needles, microwave ablation needles, HIFU delivery systems, and radiation delivery devices, or other therapeutic devices. Monitoring probes for measuring temperature or dose, etc. may also be used along with probes that perform a protective function such as cooling an area that is adjacent to a region that is being ablated using heat, etc. In some implementations (described in greater detail below), needles may further serve as elements that also restrain the anatomy from motion.

Dynamic Reference Device 315

In one implementation, system 300 may include a dynamic reference device 315 capable of tracking a patient's anatomy. Examples of dynamic reference device 315 may include, but are not limited to, a tracked Foley catheter, a skin patch (e.g., as described in U.S. Pat. No. 7,751,868 to Glossop which is hereby incorporated by reference herein in its entirety), a tracked needle, a K-wire (e.g., as described in U.S. Pat. No. 7,840,254 to Glossop which is hereby incorporated by reference herein in its entirety), etc.

Control Application 307

As previously noted, computer device 301 may host control application 307. Control application 307 may comprise a computer software application that includes instructions that program processor(s) 304 (and therefore computer device 301) to perform various processing operations.

In one implementation of the invention, control application 307 may cause computer device 301 to send, receive, and/or manipulate data regarding the anatomy of a patient, one or more objects, or other data. This data may be stored in memory device 305, or in another data storage location (e.g., the one or more databases described above). In some implementations, computer device 301 may receive live data (in real-time), or stored data. Computer device 301 may send, receive, and/or manipulate data regarding the location, position, orientation, or coordinate(s) of a position indicating element (e.g., sensor coils or other position indicating elements), or one or more other elements, received by tracking device 302. This data may also be stored in memory device 305 or in another data storage location (e.g., the one or more databases described above).

Control application 307 may further cause computer device 301 to produce, format, reformat, or otherwise manipulate one or more images, position/orientation/location data, or other data. Images may be displayed on display device 310. In some implementations, one or more live images may be displayed. Display device 310 may further display (or otherwise convey) audio data in addition to, or instead of, visual data. Such an audio display may produce tones or other indicators regarding the system.

Control application 307 may additionally cause computer device 301 to generate and display images of the anatomy of a patient along with the position or orientation of an instrument, fiducials, or both (or other information) superimposed thereon in real-time such that motion of the tracked instrument within the anatomy of the patient is indicated on the superimposed images for use in an image-guided procedure.

In some implementations, indicators (e.g., markings, lines, circles, spheres, letters, numbers or other indicators) may be produced on an image of the anatomy of a patient. These indicators may mark or identify features such as the boundaries of another image stored in memory device 305.

In some implementations, control application 307 may facilitate mapping of a target lesion (e.g., a cancerous region) or other portion of a patient's anatomy, or other operations related to a map of the target lesion or portion of the patient's anatomy. For example, control application 307 may generate and display (e.g., on display device 310) the position of a targeting template relative to a location in a target lesion, a projected path (of the target paths of the targeting template) including a path a needle or other instrument inserted into a hole of the targeting template will follow if the needle or instrument is extended past a distal end portion of the template. Control application 307 may additionally generate and display (e.g., on display device 310) a point at which a needle or other instrument placed in a hole of the template will intersect a target lesion if the projected path of the needle or instrument intersects the determined path of the target lesion, as well as an indicator of the closest approach from a needle or other instrument passing through a hole in the template to the target lesion if the projected path of the needle or instrument does not intersect tissue not intended to be treated or biopsied. Additional displays may be presented.

The foregoing system architecture is exemplary only, and should not be viewed as limiting. The invention described herein may work with various system configurations. Accordingly, more or less of the aforementioned system components may be used and/or combined in various implementations. For example, in FIG. 3, as well as in other drawing figures, different numbers of entities than those depicted may be used.

Templates

Figure 4:
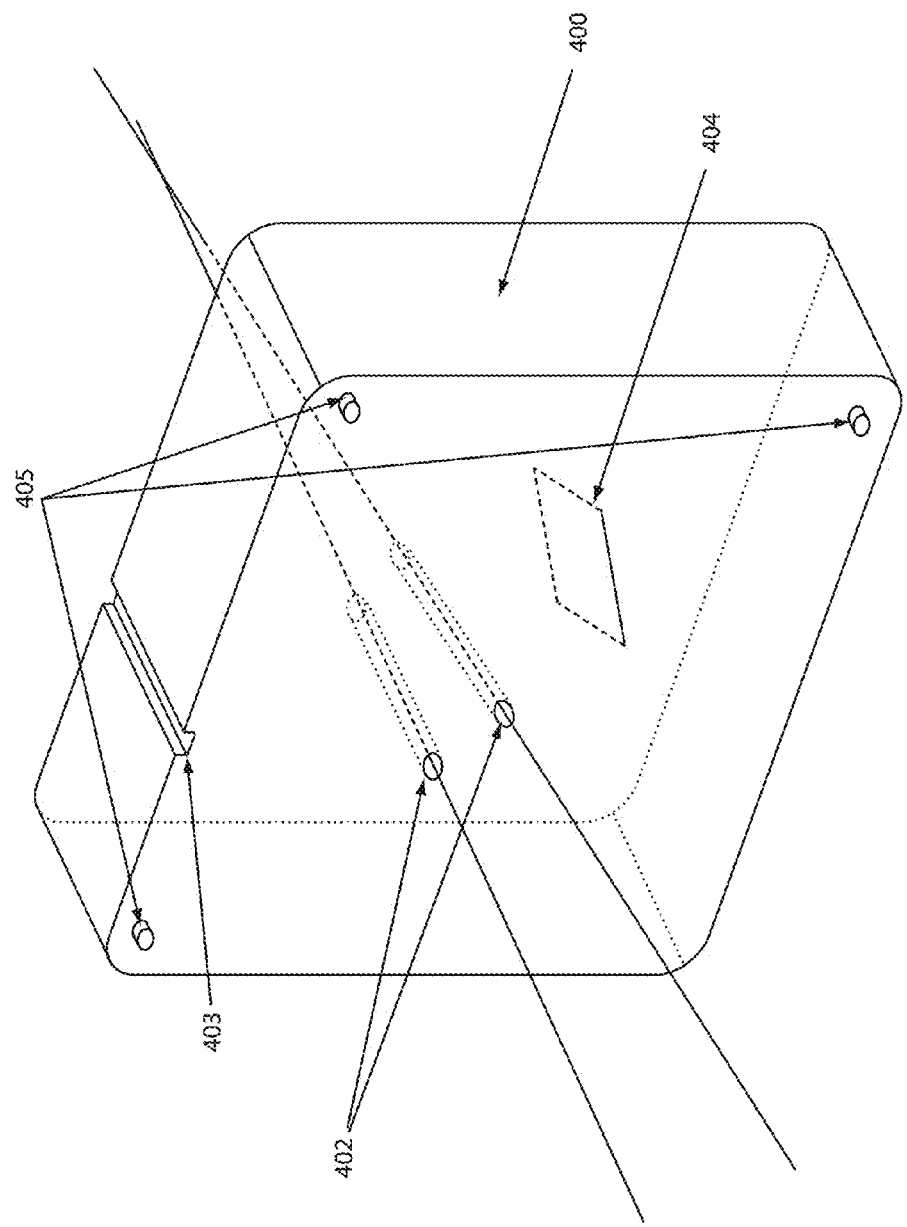
FIG. 4 is an exemplary schematic representation of a template, according to an aspect of the invention.

FIG. 4 is an exemplary depiction of a template 400 (which may also be referred to interchangeably herein as a "targeting template" or "guide"), according to an aspect of the invention.

In one implementation, template 400 may comprise a solid block of biocompatible material such as, for example, glass, stainless steel, titanium, plastics such as polycarbonate, delrin, polyethylene, polyetheretherketone (PEEK), ethylene vinyl acetate, polyphenylsulfone (PPSU), polysulfone (PSU), acrylonitrile butadiene styrene (ABS), or other material. In some implementations, template 401 need not comprise a biocompatible material if it is suitably draped (or otherwise covered) in a sterile barrier material. Although depicted as a square in FIG. 4, template 400 may have any shape. Template 400 may also comprise a curved or contoured structure.

As shown in FIG. 4, template 400 may comprise one or more guide elements 402 that extend through the body of template 400. For ease of explanation, a guide element 402 may be referred to throughout this detailed description as a "hole." It should be appreciated, however, that other similar descriptors may be used in lieu of "guide element" including, but not limited to, a trajectory, passage, or channel. Further, as used herein, a pair of holes (or openings) may be described as defining an instrument trajectory or channel. For example, a first channel that enables passage of a first medical device through a body of template 400 may be defined by a first channel opening (or entrance or hole) on a first side of the template body and a corresponding first channel opening (or exit or hole) on a second side of the body of template 400. Likewise, a second channel that enables passage of a second medical device through the body of template 400 may be defined by a second channel opening (or entrance or hole) on the first side of the template body and a corresponding second channel opening (or exit or hole) on the second side of the body of template 400, and so on. In some implementations, template 400 may have multiple channels for enabling passage of multiple medical devices through the template body.

In some implementations, one or more of holes 402 may be used for different purposes. For example, some holes may comprise defined instrument trajectories, such that instruments passing through template 400 would follow the trajectory of the holes 402. Some holes may be used for therapy devices, such as thermal ablation instruments, while adjacent holes may be used for placing devices for monitoring temperature (such as thermocouples), or even cooling devices to protect sensitive tissue from thermal damage. Still other holes may be used to inject therapeutic agents, etc. Although described and illustrated as holes for ease of reference, trajectories (or passages or channels) 402 may have any cross-section.

One or more holes 402 may be drilled into template 400 at various orientations. In one implementation, the holes 402 may be created using a Computer Numerical Control (CNC) drilling or milling machine. Alternatively, the holes may be made using electrical discharge machining or any other type of technology designed to bore or create holes. In one implementation, template 400 and holes 402 may be created using an additive technology such as a three-dimensional (3D) printing system of which multiple technologies exist.

In an implementation, template 400 may further comprise one or more locating features 403 such as channels, divots, holes, etc. Locating features 403 may be used to position template 400, or assist in mounting items to template 400.

According to an aspect of the invention, one or more cutting guides 404 may be cut into template 400 at various orientations using the technologies listed above. One or more cutting guides 404 may be used to help position a blade or saw or other flat cutting or therapy device. Although depicted in FIG. 4 as straight, cutting guide 404 may form a straight or curved path in the block through which instruments may be guided to help perform an interventional procedure in a patient by guiding the instruments.

Template 400 may further comprise one or more fiducial features (or registration features or fiducial markers) 405 for use as a point of reference or a measure. Fiducial features 405 may comprise grids, holes, cuts, or markings (having any number of shapes) that may be designed to be visible under an imaging modality. Such features may be visible when viewed by the imaging equipment alone. Fiducial features 405 may also be processed to include a contrast material so that the features 405 may be better viewed under the imaging modality. For example, a barium material may be placed in fiducial features 405 to enhance visibility under CT or X-ray. Water or gadolinium may be placed in fiducial features 405 to enhance visibility under MRI. Other materials and feature types may be used for other modalities. A further feature of fiducial features 405 is that they be configured so that a tracked probe may be touched to them so that their position in patient space may be determined.

The locations of any holes 402, locating features 403, cutting guides 404, fiducial features 405, etc. are known relative to one another and to the coordinate system of template 400.

Figure 5:
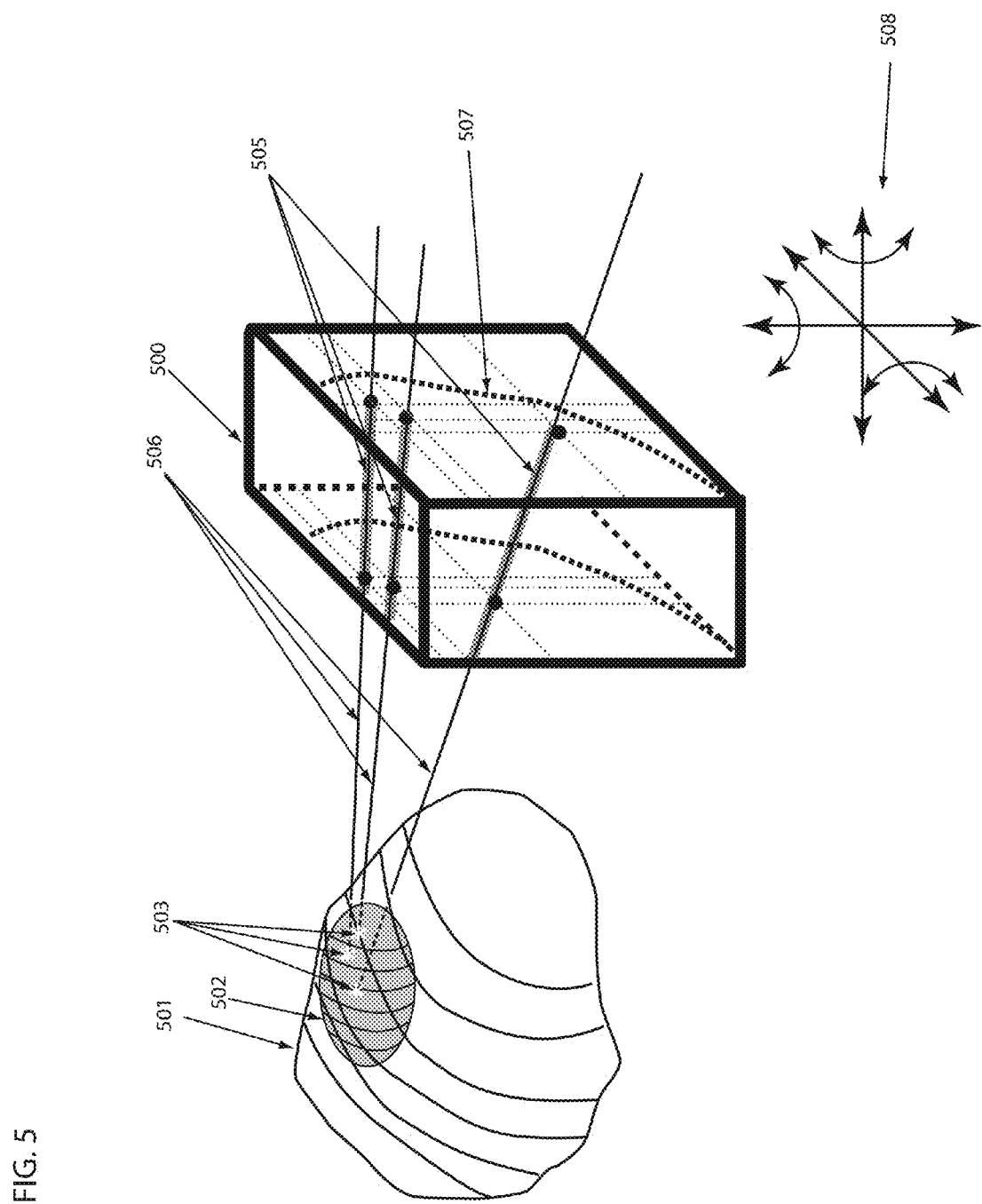
FIG. 5 is an exemplary depiction of a template used to guide instruments to predefined locations in an organ, according to an aspect of the invention.

FIG. 5 is an exemplary depiction of a template 500 used to guide instruments to predefined locations in an organ (in this example, a prostate gland), according to an aspect of the invention. FIG. 5 shows a segmented view of a prostate gland 501 obtained, for example, from pre-procedure images. It may include an area of interest 502 on which one or more targets 503 have been identified by a radiologist or other physician. In an implementation, the one or more targets 503 may be individual tumors, or locations within the same tumor that a physician may wish to treat with the goal of better treating the complete tumor.

In an implementation, template 500 may be manufactured that includes one or more holes 505 oriented such that instruments passed there-through approach the one or more targets 503 along paths 506. In designing the locations and orientation of holes 505 for template 500, it may be necessary to assume or select a location at which template 500 should be placed during the procedure. Once this is known, one or more paths 506 may be drawn from the one or more targets 503, intersecting template 500, thereby specifying the location and orientation of any holes 505 that are to be placed in template 500. This may also impact the shape of template 500, since only the designated paths 506 may need to be contained within the template, and regions such as the region to the right of line 507 that do not include any holes or paths may be removed from template 500 without affecting its behavior. Contouring template 504 in this way may offer advantages by decreasing the weight of template 500 and/or making template 500 more ergonomic, among other advantages.

In an implementation, during a procedure, template 500 may first be placed in the correct relationship (location and position) relative to prostate 501. In order to correctly hit the targets 503, this may occur during an alignment step. Instruments placed into holes (or trajectories) 505 may also be inserted to the correct depth along paths 506.

In an implementation, template 500 may be aligned to prostate 501 through one or more rotations or translated as indicated in 508. Template 500 may, for example, be moved up/down, left/right, forward/back and rotated as a roll, pitch or yaw motion, or any combination thereof.

Figure 6:
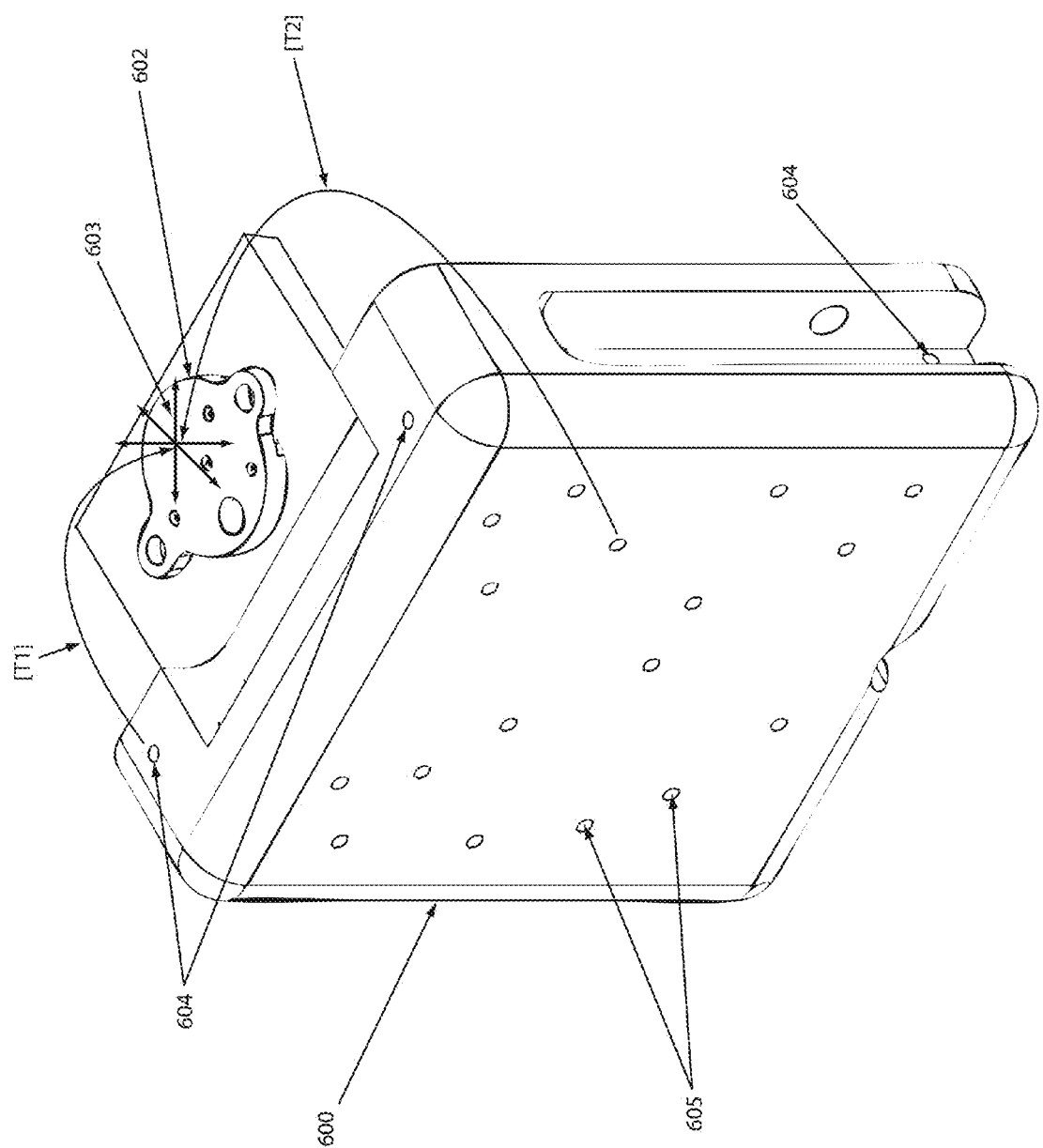
FIG. 6 is a schematic representation of a template with a position indicating element and fiducials attached, according to an aspect of the invention.

FIG. 6 is a schematic representation of a template 600 with a position-indicating element (or tracker) 602 and one or more fiducial features 604 attached, according to an aspect of the invention. Tracker 602 may be permanently affixed to (or integrated into) template 600. Alternatively, tracker 602 may be removable and replaceable in the same position on template 600. Further, tracker 602 may be permanently affixed (or releasably coupled) to a frame assembly that surrounds (or encompasses) all or a portion of template 600.

In an implementation, the location and orientation of the origin 603 of tracker 602 may be known with respect to the one or more fiducial features 604, and to template holes 605 through fixed transformations (e.g., "T1" and "T2"). As shown, T1 represents the transformation from a fiducial to the origin 603 of tracker 602, and T2 represents the transformation from one of holes 605 (that will be used for a needle or other instrument) to origin 603. A transformation (like T1 and T2) will exist for each feature on template 600 to relate origin 603 of tracker 602 to each feature. As such, the location and orientation of each hole 605 in template 600 is thus known relative to tracker 602. Therefore, when tracker 602 is queried by a tracking device (not shown), the position and orientation of tracker 602 relative to the tracking device allows the position and orientation of each of template holes 605 and fiducial features 604 to be derived in "patient space" (relative to the tracking device).

In one implementation, at least three fiducial features 604 may be used in conjunction with a probe containing a position-indicating element. The probe (not shown) may be temporarily placed into the fiducial features 604 to locate template 600, and therefore the template holes 605.

Figure 7:
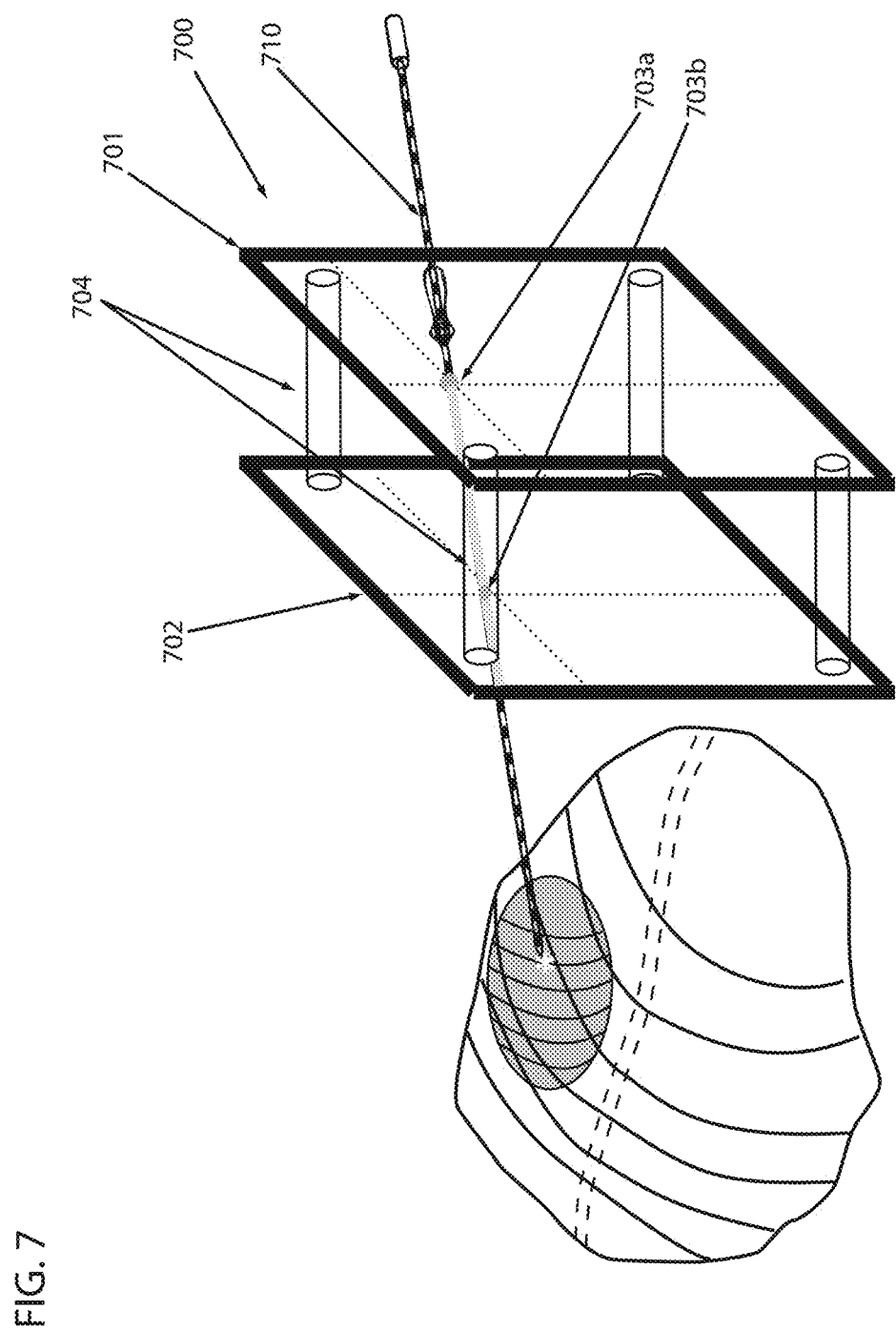
FIG. 7 is an exemplary depiction of a template composed of two plates, according to an aspect of the invention.

In one implementation, tracker 602 may be absent, and the fiducial features 604 alone may be used to locate template 600, and therefore the template holes 605. In an implementation, the template holes 605 themselves may serve as the fiducial features. In an implementation, the fiducial features 604 may be filled with a contrast agent to render them visible under an imaging modality. Although shown as holes in FIG. 6, it should be appreciated that fiducial features 604 may be any holes, lines, grids, cuts, or shapes etc., or any combination thereof Alternative Template Design FIG. 7 is an exemplary depiction of a template 700 comprised of two plates rather than the solid block of material that comprises templates 400, 500, and 600 of FIGS. 4-6, respectively.

As shown, template 700 comprises a first plate 701 and a second plate 702 separated by one or more spacers 704 such that the first and second plates (701, 702) remain at a fixed distance from one another. In an implementation, the one or more spacers 704 may comprise blocks, rods, tubes, or other shapes, or may alternatively comprise a collar that surrounds plates (701, 702) and fixes them at a prescribed distance from one another. First and second plates (701, 702) may comprise plates fabricated from one or more of the materials discussed above with regard to templates 400, 500, and 600.

According to an aspect of the invention, template 700 may comprise one or more guide element pairs that define instrument trajectories or other channels or passages. For example, first plate 701 may have an opening (or hole) 703a, and second plate 702 may have a designated, corresponding opening (or hole) 703b. Opening 703a (in first plate 701) may define an entrance for a device (or instrument) 710, while corresponding opening 703b (in second plate 702) defines an exit for device (or instrument) 710, such that device 710 can pass through plates (701, 702), and therefore template 700.

For implementations wherein template 700 comprises multiple guide element pairs (to allow for the passage of multiple devices), each respective pair of guide elements may be similarly labelled to assist a physician (or other individual) in determining which pairs of guide elements (holes) are related. As an example, first plate 701 may include a marking (e.g., "A" or "1") located near opening 703a, while second plate 702 may include the same marking (e.g., "A" or "1") located near opening 703b such that the physician (or other individual) can quickly and easily determine that openings (703a, 703b) comprise a corresponding pair of openings that collectively define the entrance and exit for a given instrument trajectory (or passage or channel).

By constructing template 700 using a pair of plates (rather than from a single block), template 700 may be lighter, more compact, and fabricated at a lower cost, using less material, and/or a lower-cost fabrication technique (e.g., by using a three-axis drilling machine instead of a more complex five-axis machine).

In one implementation, first plate 701 and second plate 702 may be constructed, for example, by printing the hole pattern on sheet(s) of paper and manually or photographically transferring the holes location to each plate, and then drilling them. In another implementation, the locations of the holes may be transmitted to another location where the plates may be fabricated by a specialized shop or piece of equipment, with the finished plates later sent to the physician performing the procedure.

In an implementation, the one or more spacers 704 may not be of equal length or diameter (unlike as shown in FIG. 7). They may also not be symmetrically placed (unlike as shown in FIG. 7).

Other possible plate configurations exist including, for example, partial plates, more than two layered full or partial plates, non-flat plates, etc.

In some instances, a respective pair of guide elements (holes) defining a trajectory (or passage or channel) may be oriented parallel to one another such that a given instrument inserted through the holes is perpendicular to the plates. In other words, opening (or hole) 703a on first plate 701 may be aligned with opening (or hole) 703b on second plate 701 such that a longitudinal axis of an instrument (e.g., device 710) inserted through the holes (703a, 703b) is perpendicular to plates (701, 702).

Figure 8:
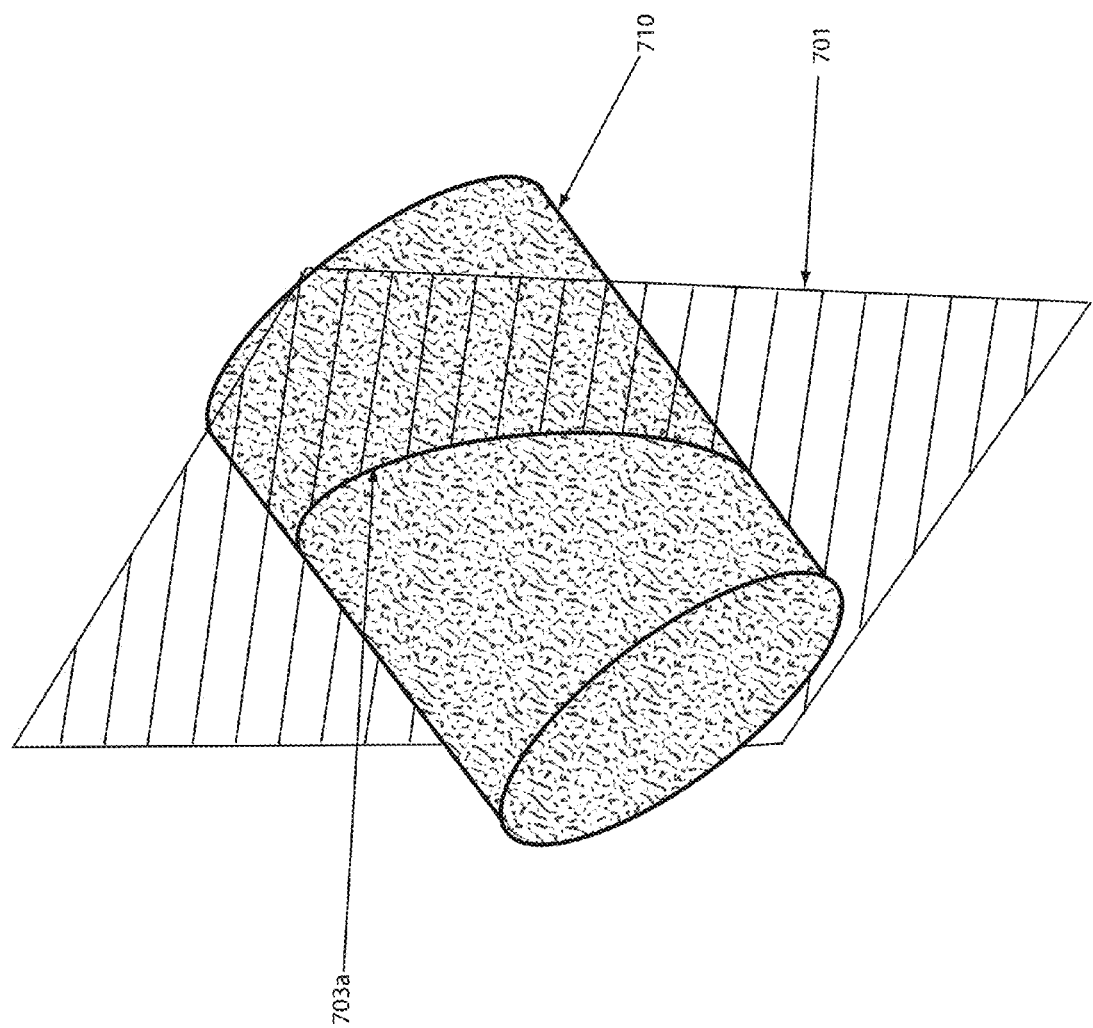
FIG. 8 illustrates an elliptical opening in a template plate to facilitate a non-perpendicular passage of a cylindrical instrument through the plate, according to an aspect of the invention.

Additionally or alternatively, template 700 may include a respective pair of guide elements (holes) defining a trajectory (or passage or channel) that is angled such that a given instrument inserted through the holes is not perpendicular to plates (701, 702), but rather extends through template 700 at an angle. In these instances, the openings (703a, 703b) in plates (701, 702) may be elliptical in shape such that that cylindrical instruments or needles (that are not intended to pass through template 700 perpendicularly to the plates) are permitted free passage through plates (701, 702), and therefore through template 700. This is illustrated in the magnified view shown in FIG. 8, where opening 703a of first plate 701 is elliptical to allow cylindrical device 710 to pass there-through. Characteristics of elliptical opening 703a (e.g., size) may be calculated depending on the angle of the instrument (e.g., device 710) intersecting the plane of first plate 701. Other instrument shapes may also be easily accommodated in this manner by creating hole 703a (and corresponding hole 703b) in the correct size and/or shape.

Although plates (701, 702) have been described as comprising planar structures, they may comprise curved or contoured structures.

Further, although template 700 comprises a pair of plates rather than being formed from a single block, it should be recognized that the various components of templates 400, 500, and 600 (of FIGS. 4-6, respectively) described in detail above (e.g., guide elements, locating features, cutting guides, fiducial features, a position-indicating element (or tracker), etc.) may also be used with template 700.

Further, although not illustrated in FIG. 7, in one implementation, plates (701, 702), one or more spacers 704, and/or other components of template 700 may be secured in place a frame assembly that surrounds (or encompasses) all or a portion of template 700.

Use of Template in a Guided Interventional Procedure

Figure 9:
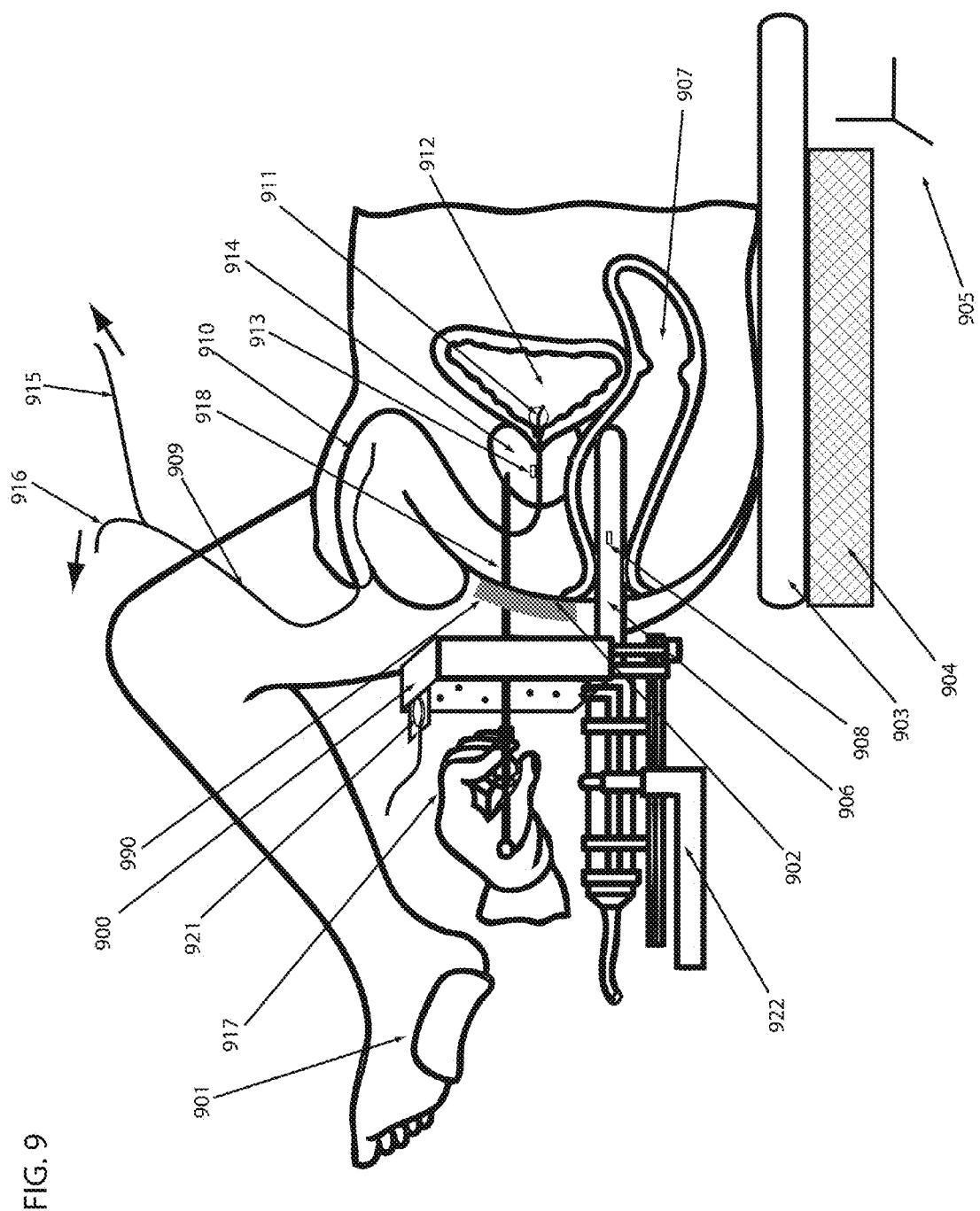
FIG. 9 is an exemplary depiction of a template used in a guided interventional procedure, according to an aspect of the invention.

FIG. 9 is an exemplary depiction of a template 900 used in a guided interventional procedure (in this case, a needle procedure), according to an aspect of the invention. In particular, FIG. 9 depicts a patient lying on an operating table 903 undergoing a procedure. The patient is shown in a lithotomy position with feet resting in stirrups 901 with the patient's perineum 902 positioned near the front of operating table 903. A position sensor 904 (such as, for example, an electromagnetic field generator or optical camera array) is positioned near the patient. A coordinate system 905 is associated with position sensor 904. In this exemplary, and non-limiting implementation, a TRUS probe 906 is placed in the patient's rectum 907 to assist in visualizing the prostate. TRUS probe 906 may incorporate a removable or permanent position indicating element 908 so that the location and orientation of the probe's scan plane is known assuming a calibration as indicated previously has been performed.

In this example, a Foley catheter 909 may be inserted into the urethra 910. At the distal end of catheter 909, a balloon 911 may be inflated to secure the catheter at the mouth of the bladder 912. On or in catheter 909, a position indicating element 913 may be positioned in the vicinity of the prostate gland 914. Wire(s) 915 from position indicating element 913 may be connected to the position sensor 904. The lumen 916 of catheter 909 may be used to drain urine from the bladder.

During a guided interventional procedure, a physician (depicted here by gloved hand 917) may use one or more instruments 918 that may optionally include a position indicating element to assist in positioning instrument 918 in a specific location in prostate 914 by directly piercing the perineum 902. In an implementation, instrument 918 may comprise a biopsy needle, hollow cannula, therapy needle such as a laser, or other device. In an implementation, instrument 918 may comprise a standard instrument that may or may not include a position indicating element.

According to an aspect of the invention, template 900 may be positioned at a predetermined distance and/or angle from perineum 902. A position indicating element 921 (similar to position-indicating element or tracker 602 of FIG. 6) may be fixed to template 900 such that it is able to track the location and orientation of template 900 with respect to frame of reference 905. In one implementation, if template 900 cannot be placed in the correct location due to interference with the patient and/or equipment, another template (if available) that was created for placement in a different assumed location may be utilized. One or more instruments 918 may be inserted through one or more holes of template 900 to a predetermined depth and into prostate 914, according to a pre-procedure plan.

In an implementation, TRUS probe 906 (or other ultrasound probe) may be affixed to a support mechanism 922. Support mechanism 922 may comprise a Biojet (D&K Technologies GmbH, Barum Germany) or the Multi-purpose Workstation LP (Civco Inc., Coralville Iowa) that may include motors and/or encoders to help position TRUS probe 906 in the patient.

In an implementation, support mechanism 922 may also hold template 900 (or a frame assembly that surrounds (or encompasses) all or a portion of template 900. In an implementation, template 900 may be moved independently from TRUS probe 906. Encoders on support mechanism 922 may report the relative location of the template 900. The position and orientation of TRUS probe 906 may be tracked using encoders on support mechanism 922. In these instances, it may not be necessary to include position indicating elements (e.g., such as TRUS probe position indicating element 908 and template position indicating element 921). In such instances, position sensor 904 may be optional unless another position indicating element (e.g., such as catheter position indicating element 913) is used.

In one implementation, template 900 may be moved into position using dials or other controls on support mechanism 922. In an implementation, template 900 may be moved into position in an automated manner using a robotic mechanism attached to support mechanism 922. In an implementation, TRUS probe 906 may be moved in a similar way.

In one implementation, perineum 902 (or another entry point) may be covered with a sterile single or multilayered membrane 990 that may comprise one or more layers of silicone, latex rubber, thermoplastic elastomer, polyvinylchloride, or other elastomeric material composited with an adhesive film. The use of membranes will be described in greater detail below with reference to FIGS. 17 & 18.

It should be appreciated that template 900 may comprise a pair of plates (e.g., such as template 700), or may be formed from a single block (e.g., such as templates 400, 500, and 600 of FIGS. 4-6, respectively).

Template Hole Variations

It may occasionally be necessary to sample in a region around an actual target point to account for system error, registration errors, organ movement, position sensor error, target selection error, needle deflection error, or other issues that may render needle targets not exactly correct. Further, a target may be large or poorly defined, and it may be desirable to sample an area around the focus of a target.

Figure 10:
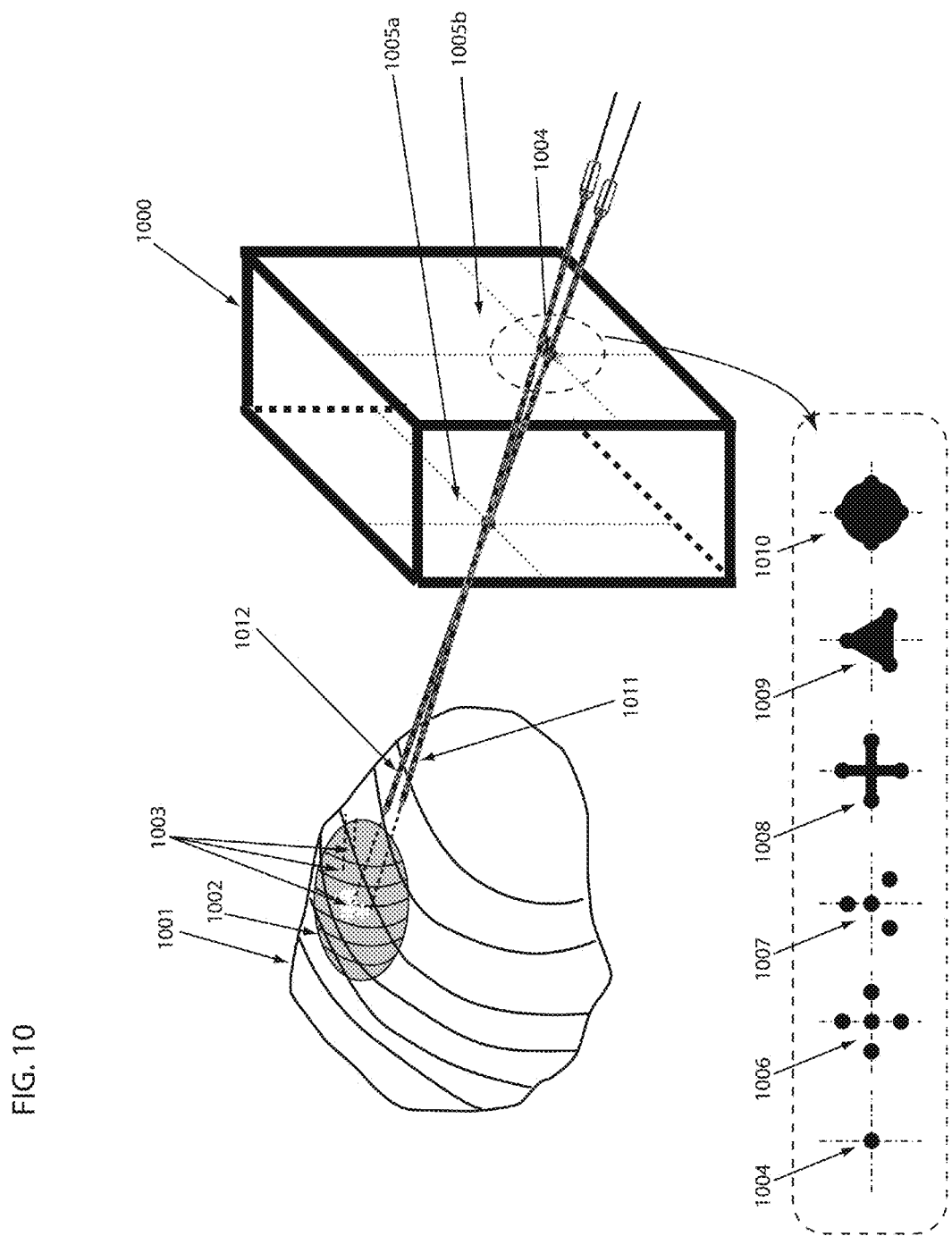
FIG. 10 illustrates how variations on an entry hole on a template may be used to sample a region around a target location, according to an aspect of the invention.

FIG. 10 depicts a situation where it may be desirable to sample multiple locations 1003 in the vicinity of a target 1002 within an organ 1001. Accordingly, in one implementation, one or more guide elements (e.g., holes) 1004 in one or more of the plates (1005, 1005*b*) comprising template 1000 may be manufactured as a cluster of holes (e.g., 1006, 1007), a cross-shaped hole 1008, a triangular-shaped hole 1009, an enlarged hole 1010, or any other grouping of holes, or enlarged shape, or shape with different cross-sections, such that an instrument (e.g., needle) 1012 can systematically take multiple different trajectories, one (non-limiting) example of which is indicated as 1011. This enables multiple samples to be taken near the same location. One or both of plates (1005*a*, 1005*b*) may be modified in this way. In the case of a modification in only one of the plates (e.g., 1005*b*), the hole in the second plate (e.g., 1005*a*) may need to be enlarged or otherwise modified to accommodate the larger range in trajectories. Multiple depths may also be specified.

In those implementations wherein a block template is used (e.g., such as templates 400, 500, and 600 of FIGS. 4-6, respectively), cavities may be fabricated within the block (using for example rapid prototyping or milling operations) that permit oversampling in a region as described above through creation of an appropriately shaped cavity, for example a conical shape with the cone base positioned at the entry point of the instrument and the cone tip at the exit of the instrument. The cavities in the block may be also be comprised of curved or other shaped pathways which may be advantageous in obtaining a beneficial trajectory of a flexible instrument to the target.

Deployable Restraining Device(s)

In some instances, an organ undergoing therapy or biopsy (or another procedure) may move during the procedure. In such instances, it may be advantageous to either restrict the motion of the organ, or track its motion in order to compensate for its motion. Accordingly, in an implementation designed to track and/or restrict the motion of the organ, one or more restraining devices may be employed to "pin" (or otherwise secure) an organ in place by using devices such as needles to affix it. The one or more restraining devices may be removable and repositionable, and may be designed to engage the tissue or organ (e.g., such as the breast or prostate) through a hook, suture, balloon, or catch and restrict its motion by anchoring it to another type of tissue such as skin or bone, or to the externally placed device such as a template. In an implementation, devices such as a Hawkins I or Hawkins II or Homer needles (Argon Medical Devices, Plano Tex.) among others, may be employed. A Foley catheter may also be employed.

Figure 11:
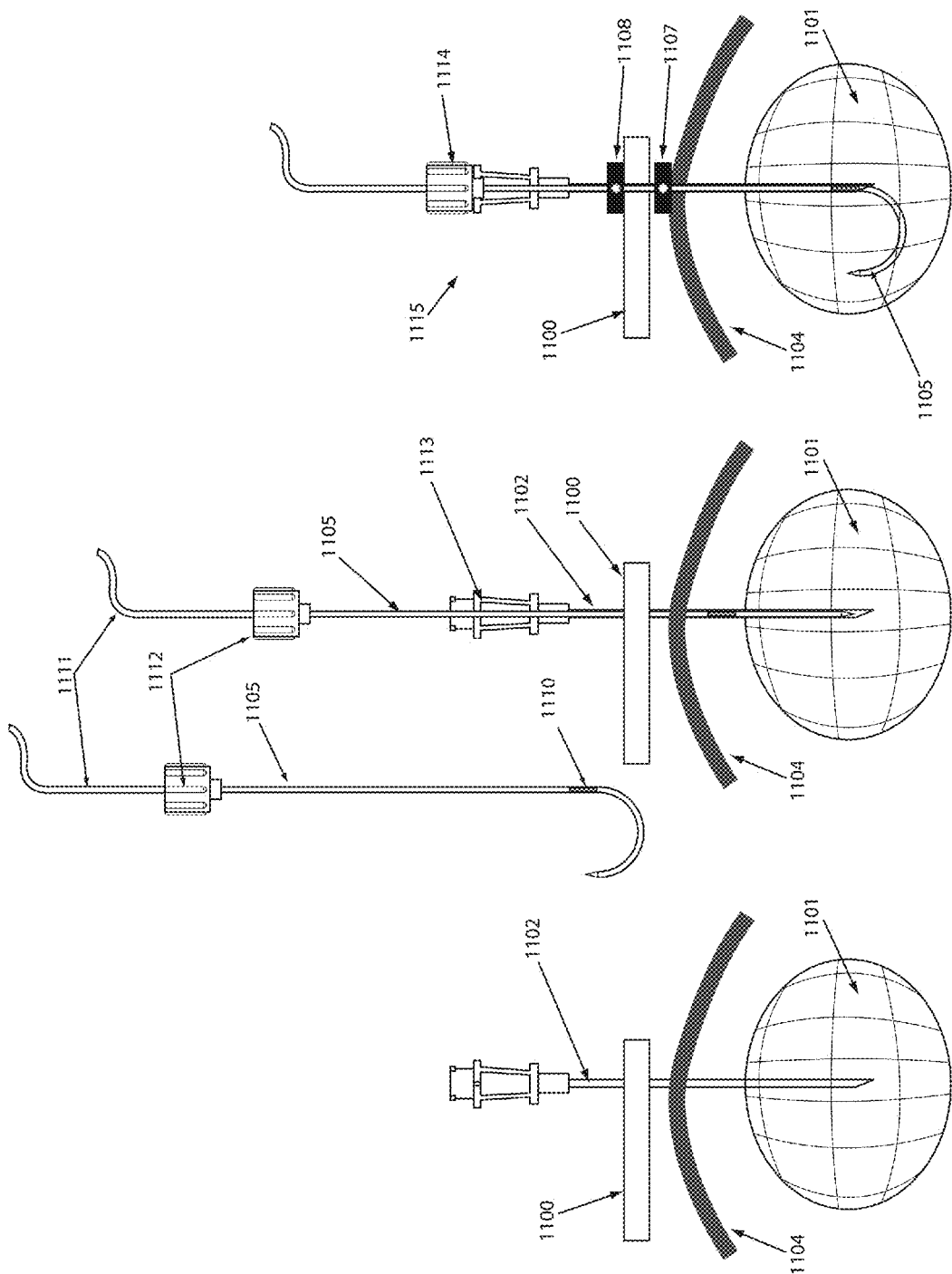
FIGS. 11A-11C are exemplary depictions of a deployable restraining device that can restrain tissue and also serve to track its motion, according to an aspect of the invention.

FIGS. 11A-11C are exemplary depictions of a deployable restraining device (e.g., a hook needle) that can restrain tissue and also serve to track its motion, according to an aspect of the invention. While FIGS. 11A-11C depict a single restraining device (for ease of illustration), it should be appreciated that multiple restraining devices may be used simultaneously.

As shown in FIG. 11A, a tissue 1101 is penetrated by a cannula 1102. The cannula may pass through a template 1100, and a tissue layer 1104 (e.g., such as skin).

As shown in FIG. 11B, a needle 1105, is then passed into cannula 1102. Needle 1105 may have a releasable barb or, as illustrated here, may be pre-formed using a shape memory alloy (SMA) or super-elastic material (e.g., such as nitinol) so that it achieves a hook shape when not constrained by cannula 1102. In FIG. 11B, needle 1105 is shown in its "natural," unconstrained state. When introduced into cannula 1102, needle 1105 temporarily straightens.

As shown in FIG. 11C, needle 1105 is advanced through cannula 1102 and reestablishes its natural hook shape as it is deployed, securing it in the tissue. The hub 1112 of needle 1105 and the hub 1113 of cannula 1102 may be connected using for example a Luer lock forming a cannula/needle assembly 1114. To restrain the tissue, a locking device 1107 may be used to engage a tissue layer (e.g., such as the skin surface 1104 or bone). If the cannula/needle assembly 1114 is then fastened to the locking device 1107, the tissue secured by the hook is restricted from moving relative to the tissue used to secure it (e.g., tissue 1104).

In another implementation, a locking device is placed against template 1100 as illustrated by numeral 1108 instead of 1107.

In either case, the locking device 1107 or 1108 may function by gripping tightly to the needle or cannula and simultaneously pressing against template 1100 or tissue layer 1104. This effectively immobilizes tissue 1101 secured by needle 1105. In an implementation, locking device 1107 or 1108 may be a releasable collet, clip or other clamp that may be tightened on needle 1105 or cannula 1102. The combination of needle 1105, cannula 1102 and locking device 1107 may be collectively referred to as a "restraining device," (numeral 1115 in FIG. 11C).

In an implementation designed to track the motion of the tissue or organ for dynamic referencing or gating, one or more such restraining devices may be constructed that incorporate one or more position indicating elements that may be used to monitor the position of the object into which it is inserted. Such a device is described, for example, in U.S. Pat. Nos. 6,785,571 and 7,840,251 to Glossop, each of which is hereby incorporated by reference herein in its entirety. An exemplary position-indicating element 1110 is illustrated in FIG. 11B. Here the position sensor is connected to position-indicating element 1110 using cable 1111.

In one implementation, the one or more restraining devices 1115 may incorporate a temperature sensor placed within it, so that the temperature of the tissue or organ that it contacts may be measured. This may be particularly important in determining the effect of a thermal or cryogenic ablation process such as cryoablation, radio frequency ablation, laser assisted ablation, microwave ablation etc.

Other types of sensors may also be used together with the restraining device 1115 to measure other properties of tissue, or progress of processes used to treat the tissue. These may include, without limitation, optical sensors, radiation sensors, pressure sensors, acoustic sensors, chemical sensors, electrical sensors, etc. Therapy devices may also be incorporated within the one or more restraining devices 1115 to deliver heat, drugs, etc.

In an implementation, the one or more restraining devices 1115 may incorporate a plurality of sensor types such as, for example a temperature sensor and/or a position sensor. In an implementation, the one or more restraining devices may incorporate a plurality of hooks to better restrain the tissue and any sensors.

Figure 12:
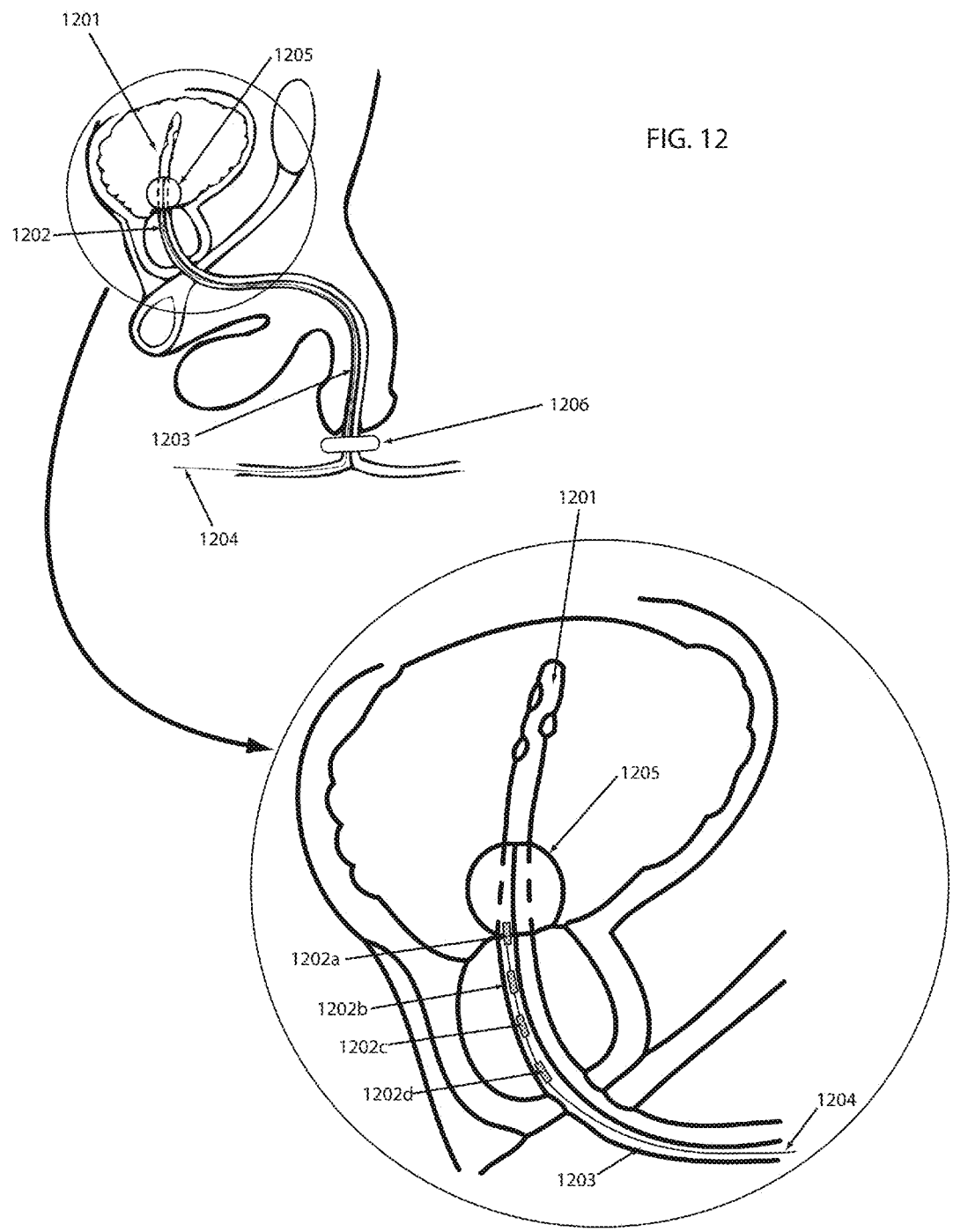
FIG. 12 is an exemplary depiction of a catheter including a position-indicating element that can be used to track motion of a tissue or organ, according to an aspect of the invention.

FIG. 12 is an exemplary depiction of a catheter including a position-indicating element that can be used to track motion of a tissue or organ, according to an aspect of the invention.

In an implementation, a catheter 1201 (e.g., a Foley catheter) may be positioned in a patient and inflated in order to immobilize a tissue or organ (e.g., the prostate) as indicated in FIG. 12. The inflation balloon 1205 normally used to retain the catheter may also serve to immobilize the prostate. A dual balloon Foley catheter such as a Coleman or Lerman catheter (C. R. Bard, Inc., Murray Hill, N.J.) may also be used (not shown). One balloon may be inflated in the urethra to restrain it, while the second may be inflated at the bladder neck.

In an implementation designed to track the motion of the tissue or organ for dynamic referencing or gating, the Foley catheter above may be equipped with a position-indicating element such as that described in U.S. Pat. No. 8,948,845 to Glossop et al. which is hereby incorporated by reference herein in its entirety. This would enable the catheter to be used in order to track the location of the prostate during the procedure. In an implementation, the Foley catheter above may serve the dual function of immobilizing the tissue and tracking any motion that occurs.

In the implementation illustrated in FIG. 12, catheter 1201 may include a position-indicating element 1202. In an implementation shown in the inset of FIG. 12, a plurality of position indicating elements 1202*a*, 1202*b*, 1202*c*, and 1202*d* may be included within catheter 1201. Position indicating elements 1202 may be located using a tracking device for purposes of dynamic referencing and registration as detailed below. In an implementation, the position-indicating elements may be attached within one of the existing lumens of the catheter, such as a balloon inflation lumen, the drainage lumen, or in an irrigation lumen of a three lumen catheter, or in a special dedicated lumen, here indicated as 1203.

In a similar manner, electrical cables 1204 may be threaded through a lumen. The position-indicating elements may be contained in a tube that is inserted into one or more of the lumens of catheter after the catheter has been placed rather than being integrated in the catheter. In an implementation, a catheter locking device 1206 may be present to help constrain the catheter and balloon from moving.

In an implementation, a catheter 1201 such as the one depicted in the inset of FIG. 12 that includes multiple position indicating elements (1202*a*, 1202*b*, 1202*c*, 1202*d*) may be used to perform a patient-to-image registration. This can be done if a pre-procedure image set (such as an MRI) of the patient into which the catheter is later inserted is available, and details of the construction and placement of each of the multiple position indicating elements is known.

In an implementation, the positions in which each position-indicating element (1202*a*, 1202*b*, 1202*c* and 1202*d*) has been secured in catheter 1201 is known relative to balloon 1205 of catheter 1201 at the time of manufacture. When catheter 1201 is inserted into the patient and balloon 1205 is inflated, the approximate location of each position indicating element within the pre-procedure images of the prostate may be deduced because:

(a) The linear displacement of each position indicating element relative to the bladder neck is known since balloon 1205 is lodged against it; and (b) The path of the urethra and thus catheter 1201 through the prostate is known from a pre-procedure MRI scan.

Therefore, if the path of the urethra is determined from scans taken prior to the operation, the position and orientation of the position indicating elements may be deduced in image space. The locations and orientations of the position indicating elements may be determined by the position sensor in patient space. This allows a registration to be performed relating the position indicating elements positions (patient space) and orientations and the assumed positions from the pre-procedure scans (image space). This registration may be used to target any device that contains a position indicating element.

In a more general form, a catheter including a plurality of position indicating elements (either built-in, or temporarily placed) may be used to register any lumen that it is placed in as long as:

(a) Locations of the plurality of position-indicating elements in the catheter is known;

(b) The catheter is placed at a known location in the patient anatomy; and (c) The path of the catheter is constrained to follow a lumen visible on the images.

Since the location of the position-indicating elements in the images can be inferred by the known geometry of the lumen and the known location of the origin of the catheter and the known location of the position-indicating elements within the catheter, they may be used to perform the registration. In an implementation, this method may be used to register anatomy with lumens such as the lungs, and vascular organs, for example.

Exemplary Flowchart

Figure 13:
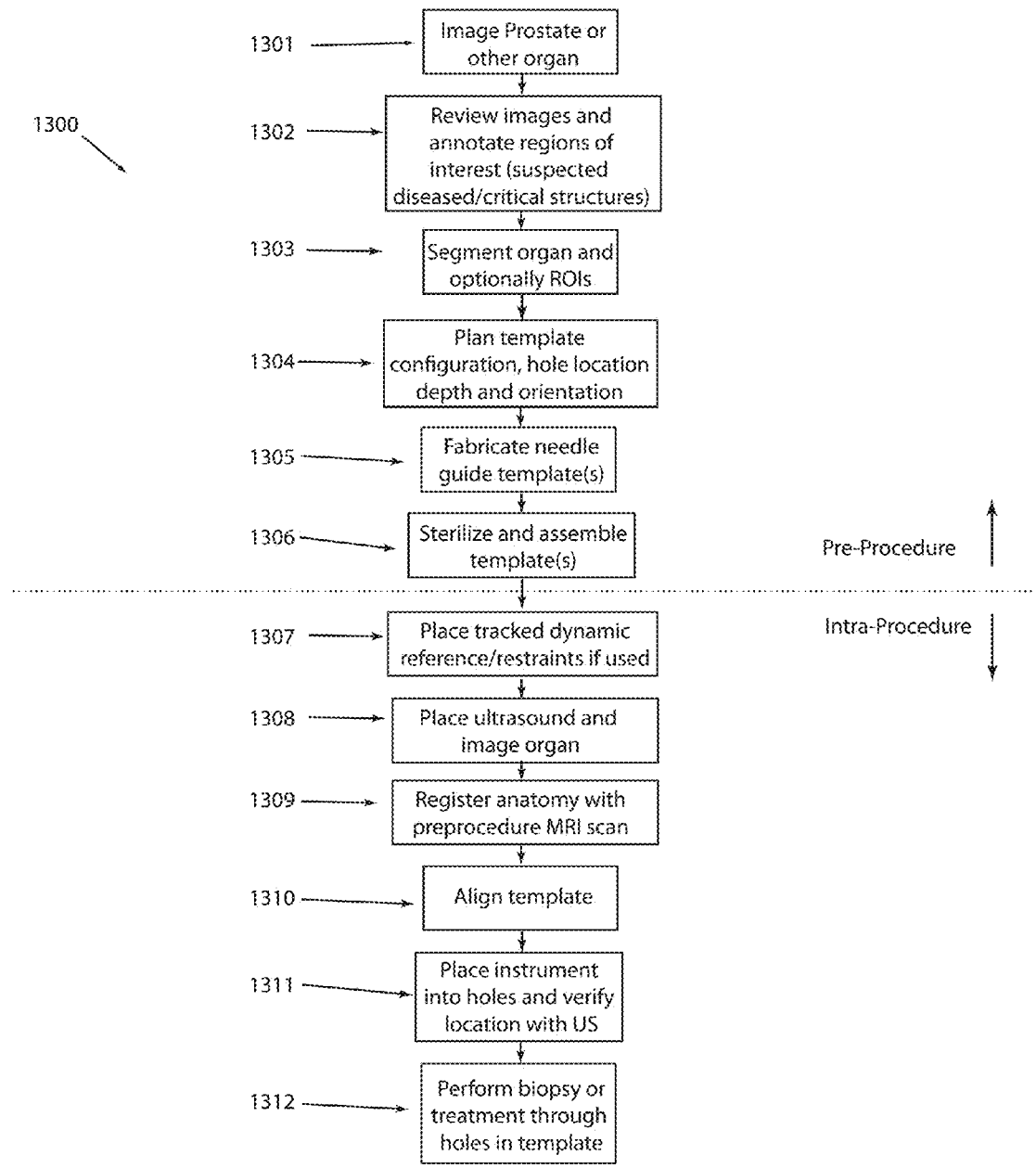
FIG. 13 is an exemplary flowchart of processing operations for creating and using a template in a guided interventional procedure, according to an aspect of the invention.

FIG. 13 is an exemplary flowchart 1300 of processing operations (or steps) for creating and using a template in a guided interventional procedure (e.g., placing a needle or other instrument for performing a biopsy, placing fiducials, or performing a therapeutic (or other) procedure), according to an aspect of the invention. Flowchart 1300 is divided into two sections, comprising a set of pre-procedural steps, and a set of intra-procedural steps.

The described steps may be accomplished using some or all of the system components described in detail above and, in some implementations, various steps may be performed in different sequences and various steps may be omitted. Additional steps may be performed along with some or all of the steps shown in the depicted flow diagram. One or more steps may be performed simultaneously. Accordingly, the steps as illustrated (and described in greater detail below) are exemplary by nature and, as such, should not be viewed as limiting.

Pre-Procedural Steps

In a step 1301, an imaging modality such as an X-ray, MRI, CT, ultrasound, tomosynthesis, PET, or other imaging modality may be used to obtain one or more two-dimensional (2D) or volumetric images of a patient's anatomy. This may take the form of contrast-enhanced, multi-parametric, or other variation of the scan or scans. The images may be formed into a three-dimensional (3D) image stack which shows details of the anatomy from many slices.

In a step 1302, the scan(s) may be reviewed by a radiologist or other specialist, or processed by a Computer Aided Diagnosis (CAD) program, or other software (e.g., control application 307). One or more targets may be annotated along with critical structures (e.g., the urethra, nerves, vessels, bones such as ribs, etc.). This information (target(s) and structure(s) or other information) may be annotated on the images, as a separate list of points and volumes, or stored in a database (or memory) along with other information, for example. Targets may also include a selection of targets designed to represent an orderly and representative sampling through an organ as might be desired during a sextant-style or saturation-style biopsy of, for example, the prostate which aims to sample from throughout the gland. Other targets may cluster more densely around certain structures deemed to be important for either therapy or biopsy such as, for example, local dose boosting around a suspected tumor whilst placing radioactive brachytherapy seeds. Yet another non-limiting example is an optimized treatment pattern for a large tumor to be treated by multiple successive or simultaneous thermal or cryoablations.

In a step 1303, the scan(s) may optionally be segmented to outline the organ of interest and/or regions of interest (ROI). This information may be annotated on the images, as a separate list of points and volumes, or stored in a computer database (or memory) along with other information, for example. This information may be used for registration among other things. In some implementations, step 1303 may be combined with step 1302.

In a step 1304, a mathematical model of a template (or "virtual template") may be generated (e.g., using control application 307) from the information gathered in steps 1302 and 1303. At the time of intervention, the template may first be assumed to be positioned and oriented in one or more locations. These assumed positions and orientations may then be replicated during the intervention procedure by placing the template in the one or more locations during the procedure. Paths to targets may then be generated from the target either automatically or manually such that they pass through the template. Multiple approaches that pass through the template may be possible, such that those that avoid critical structures (e.g., annotated during step 1302) are preferentially selected. Paths may also be selected so they are not too close together, or are otherwise more convenient for the actual procedure. The intersection of these paths with the template may be calculated, and the path through the template may be generated. This may continue for all of the targets selected in steps 1302 and 1303, or for any additional targets. Details of this planning procedure are set forth in greater detail below in reference to FIGS. 14A-14D.

In one implementation, multiple separate templates may be fabricated. Each template may, for example, be designed to be placed in a different location from the other in case the selected positioning of the initial template is not easily accessible for the particular patient setup encountered during the actual medical procedure. In such an instance, a different template may be selected that would be placed in a slightly different location that allows the procedure to be more easily performed. The multiple templates if used may also be placed in the same position in the case of extremely complex plans for example, in which a subset of treatment holes or paths would be drilled into each template. In this case multiple templates may be manufactured and so mathematical models of the various templates should be generated.

In a step 1305, the template(s) may be fabricated based on the mathematical model(s) generated in step 1304. The fabrication step may use the information generated in step 1304 to produce a template consisting of a single block (e.g., templates 400, 500, or 600) or two or more plates (e.g., template 700) that may be later connected using a spacer. Fabrication may occur using a computer numerical control (CNC) milling machine in which an automating machine is programmed to drill template holes at the correct location and orientation into one or more template "blanks" that does not contain any holes. In an implementation, fabrication may take place using an additive manufacturing process such as 3D printing. In an implementation, multiple templates may be fabricated for placement at different locations during the procedure in case a block is not easily positioned in the location initially selected. As previously noted, the template may be manufactured from any acceptable material that may be easily machined and sterilized and is compatible with the procedure. For example, the template may be manufactured from a biocompatible material that may be sterilized without causing a dimensional change to the template. In an implementation, fabrication may occur at a specialized manufacturing facility, and the finished parts may be delivered to the physician for the procedure. In an implementation, fabrication may could occur within the hospital. Additional details on the fabrication of the template are discussed below in reference to FIG. 15.

Templates may be tested for accuracy by, for example, simulating the intervention to ensure that instrument(s) will pass through the template to the correct location(s). Various forms of simulation are possible including, for example, optically shining a laser or light through the holes, or passing an instrument for example in conjunction with a tissue surrogate or "phantom" manufactured using a rapid prototyping method from a pre-operative scan so as to simulate the actual medical intervention.

In a step 1306, the template(s) created in step 1305 may be sterilized and packaged using a suitable microbial barrier material such as a Tyvek® peel-pouch. The template(s) may then be transported to a procedure room when required for the interventional portion of the procedure.

Intra-Procedural Steps

During a procedure, in a step 1307, a patient may be optionally equipped with a dynamic reference such as a tracked Foley catheter or tracking needles, or other dynamic reference device or system. Restraining devices or needles may also be placed in the patient to help fix the organ undergoing intervention, as discussed in detail above with reference to FIGS. 11A-11C.

In a step 1308, a TRUS or ultrasound (or other imaging modality) may be introduced and the prostate or other organ may be imaged. In an implementation, the template may be attached to a support mechanism that allows it to be positioned through fine adjustments of positioning knobs or dials (or other controls), or through a robotic positioning system.

In an implementation, the imaging probe may be handheld. The imaging probe (e.g., US probe) may have multiple scan planes such as the BK 8188 triplane probe (BK Medical, Peabody Mass.). In an implementation, the probe may have a position indicating element attached thereto such that the location of the scan plane(s) is known at all times. The probe may be calibrated so that knowledge of the scan probe location and image on the scan can determine the location in patient and image space of any point in the scan image.

In a step 1309, the anatomy may be registered with the pre-procedure image(s). This may be accomplished using methods that have been discussed previously, so that the transformation between "patient space" and "image space" is known.

Additionally, a type of manual registration may be performed by moving the ultrasound probe until the image from the ultrasound best matches that of the pre-procedure image. Once that is achieved, the images may be "locked" (e.g., when the probe is moved, the pre-procedure image is reformatted along the same plane as the ultrasound). Other methods involve identification of items on both the ultrasound and on the pre-procedure scan, finding the best fit of an ultrasound sweep of the prostate, etc. Other methods of registration are possible such as the Foley catheter method previously discussed.

In a step 1310, the template may be aligned to the preplanned position. This location may, for example, be set by monitoring the position indicating element on the template (if used), or by moving the mechanical positioning system until the template is in the position and orientation that was determined in step 1304. In step 1304, the preplanned position of the template was determined in image space. As the transformation between image space to patient space is known from the registration in step 1309, the preplanned position of the template can be transformed into patient space. Thus, the position that the template should be placed in is known in patient space and it may be aligned to this position. Methods for aligning the template are described in additional below in reference to FIG. 16.

In one implementation, a custom mold, vacuum cushion, or other positioning system may be used at the time of the scan in step 1301, allowing repeatable patient positioning at the time of the intervention thereby obviating the need for tracking the template.

In a step 1311, an instrument (e.g., a needle) may be introduced into hole(s) in the template. The instrument location may be used to verify that the template is aligned correctly. In an implementation, the location at which the needle would appear if correctly introduced in the template may be predicted and displayed as a graphic overlay on the live ultrasound image. If the actual image of the needle and the graphic overlay of the predicted needle location match up, then the system is aligned and the remaining needles may be introduced. If not, the template may be realigned (re-registered), and checked again.

Accuracy may also be verified using targets or fiducials placed on the skin. These may be annotated as "targets," and templated paths may be generated. Needles placed in the paths would touch the fiducials in cases where the system was performing correctly. Tracked needles may also be used and their locations compared to the planned path. Other means of verifying the correctness of the template and positioning of the template are also possible.

When inserting a device such as a needle, the depth of insertion is known from step 1304. In an implementation, the system may report the insertion depth to the physician. This information may be communicated to the physician via a display, so that the physician may mark or place a "needle stop" on the needle prior to insertion. In an implementation, the physician may observe the needle location on the ultrasound to ensure it is at the correct depth. In an implementation, if a tracked needle is used, the system may report the depth.

In a step 1312, the procedure may continue with instrument(s) being introduced into the hole(s) set in the template to the prescribed depth, and the procedures may be performed until complete. In an implementation, multiple instruments may be inserted simultaneously, or one instrument may be inserted at a time.

In one implementation, the template may be preserved for subsequent procedures at a later date (e.g., to re-biopsy locations that have been biopsied or treated, to re-treat partially treated areas, to treat areas that have been further verified under another imaging modality, etc.).

Positioning a Template and Generating Paths

FIGS. 14A-14D are exemplary depictions of method steps for positioning a template, and for generating paths through the template, according to an aspect of the invention. The following description elaborates on planning step 1304 described above with reference to FIG. 13. The described steps may be accomplished using some or all of the system components described in detail above and, in some implementations, various steps may be performed in different sequences and various steps may be omitted. Additional steps may be performed along with some or all of the steps shown in the depicted flow diagram. One or more steps may be performed simultaneously. In general, these steps may be performed on a computer device (e.g., computer device 301) that is capable of displaying and manipulating graphical objects. Accordingly, the steps as illustrated (and described in greater detail below) are exemplary by nature and, as such, should not be viewed as limiting.

In the example set forth in FIG. 14A, a tissue (e.g., prostate) 1401 is imaged as previously described (e.g., as one or more of MR, CT, multi-parametric, MRI, etc.). The following steps may be used to plan the position and orientation of a template, and generate one or more paths through it.

(1) First, one or more targets 1402 (e.g., lesions) may be identified on the scan.

(2) Next, a representation of the plates 1405 of a template (only a front plate is shown in FIG. 14A) is generated on the computer display (e.g., display device 310). These plate representations may be rotated or moved in the display.

(3) A "virtual probe" 1408 may be created on the display that is perpendicular to the front plate at its center (although any convenient location or orientation may be selected). In an implementation, the length of virtual probe 1408 is set to a distance of "d" cm (or other unit of measure) from the origin of the plate, and made perpendicular to the plate. The length of virtual probe 1408 may typically fall in the range of 1-2 cm., although any length may be used. The virtual probe remains perpendicular to the plates for the remainder of the operations.

(4) Next, a point may be selected on, for example, a graphic representation of the surface of the skin 1404 as a "pivot point" 1403. The pivot point may roughly represent the location at the center of the operative field.

(5) Plates 1405 (which may be locked together) and virtual probe 1408 may then be translated such that the tip of virtual probe 1408 is located on pivot point 1403. The orientation of plates 405 is preserved as set in step (2), but any applied translation is lost. In an implementation, the orientation relative to coordinate system 1406 selected prior to selection of pivot point 1403 is preserved.

(6) At this point, the plates 1405 may be "locked" to the pivot point, and any rotation occurs around pivot point 1403 as if the plates 1405 were pivoting on the tip of virtual probe 1408. As shown in FIG. 14B, for example, the rotation of plate 1405 from position 1405a to position 1405b is shown to occur about pivot point 1403.

(7) If pivot point 1403 is moved, as shown in FIG. 14C, the plates and virtual probe 1408 may be moved, but not re-oriented. This is shown in FIG. 14C as the plates being translated from position 1405c to 1405d, and concomitant translation of the pivot point from position 1403 to 1403a. Similarly, if the plates are translated, the virtual probe and pivot point are translated in the same manner.

(8) If the plates are to be translated, as shown in FIG. 14C, the new pivot point 1403a is established, however the distance "d" remains the same, and subsequent rotations will occur around new pivot point 1403a.

(9) Next, as shown in FIG. 14D, various trajectories 1410 may be established through the plates intersecting targets 1402.

(10) The orientation of the plates, the paths of the various trajectories 1410, the location of the pivot point 1403, and the position of the holes to be drilled 1411 in plates 1405 to obtain the trajectories may be recorded.

Although it has been assumed that the virtual probe is perpendicular to the plates, it is understood that any known fixed angle may be used. Although the foregoing method is described with reference to plates, it is understood that the same method may be used for the block form of the template (e.g., such as templates 400, 500, and 600 of FIGS. 4-6, respectively).

Template Fabrication

Figure 15:
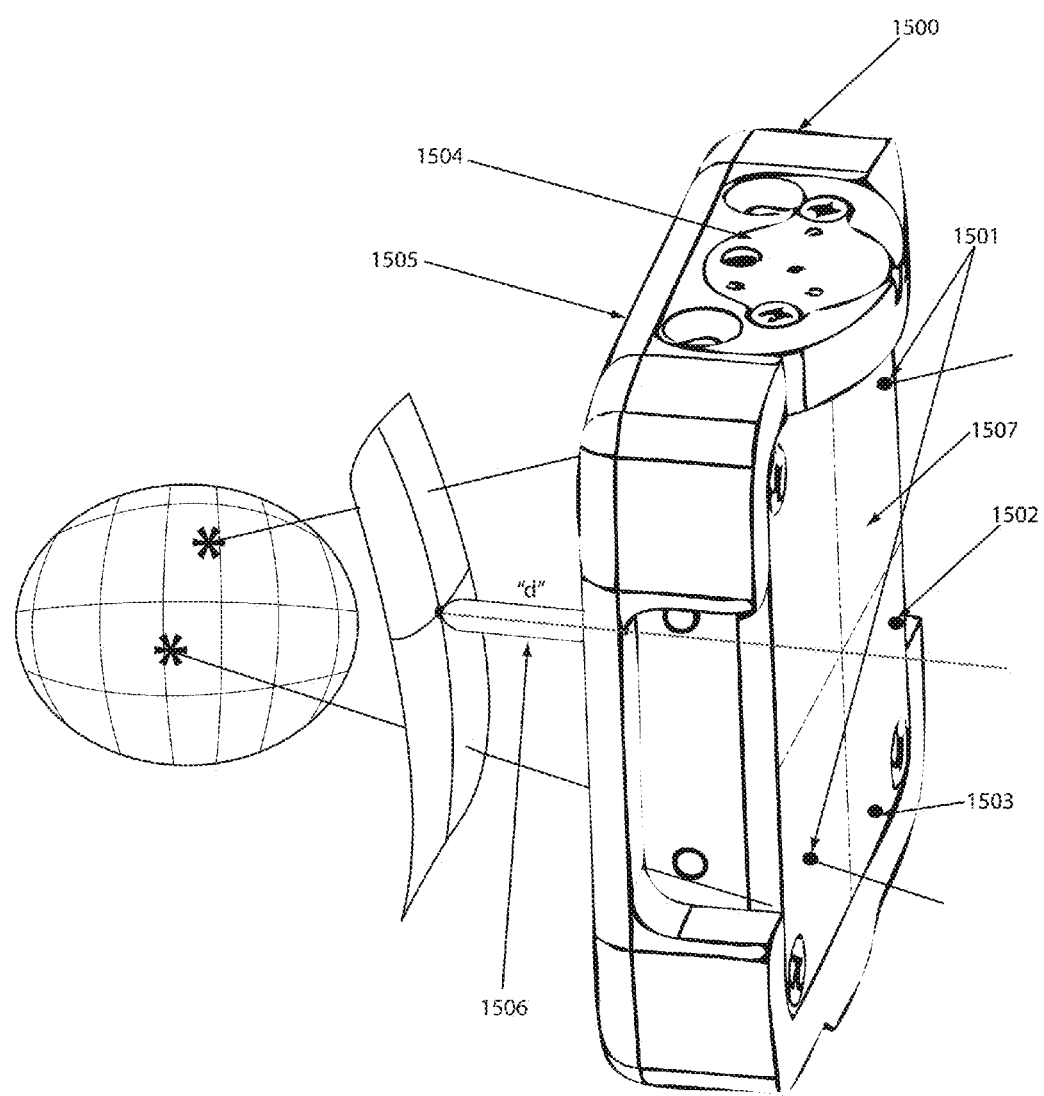
FIG. 15 is an exemplary depiction of a template with an extension post that may assist in positioning of the template in a planned position and orientation, according to an aspect of the invention.

FIG. 15 is an exemplary depiction of a template 1500 with an extension post 1506 that may assist in positioning of template 1500 in a planned position and orientation, according to an aspect of the invention. The following description elaborates on fabrication step 1305 described above with reference to FIG. 13. The described steps may be accomplished using some or all of the system components described in detail above and, in some implementations, various steps may be performed in different sequences and various steps may be omitted. Additional steps may be performed along with some or all of the steps shown in the depicted flow diagram. One or more steps may be performed simultaneously. Accordingly, the steps as illustrated (and described in greater detail below) are exemplary by nature and, as such, should not be viewed as limiting Prior to performing a guided interventional procedure, a template 1500 comprising a pair of plates may be fabricated according to determined specifications, and aligned as follows.

(1) First, one or more holes may be drilled through the plates (comprising template 1500) at the locations representing the intersection of the target trajectories through the plates as has been described earlier. Additional holes may be drilled to accommodate thermocouples or other sensors, or for devices to assist in fixating the organ. The drilled plates (the back plate 1507 is shown here) may then be attached to a plate assembly or frame 1505 as shown in FIG. 15. A position-indicating element (or tracker) 1504 may be rigidly affixed (or releasably coupled) to plate assembly or frame 1505. As shown, trajectory holes are marked as 1501, while additional holes are marked as 1502 and 1503. The location of holes 1501, 1502, and 1503 are exemplary and may, of course, differ for different templates.

(2) An extension post 1506 (having a length "d") may be affixed to the center of the front plate, as determined during the planning phase.

(3) During the interventional procedure, plate assembly or frame 1505 may be moved to the position that was determined during the planning phase by moving plate assembly or frame 1505 while taking measurements of the tracker location and orientation. Plate assembly or frame 1505 may be moved via a support mechanism (described above) that is coupled to plate assembly or frame 1505. When the difference between the tracker position and orientation and the planned position and orientation is close to zero, the assembly may be locked in that location and the procedure performed.

Although it has been assumed that the extension post 1506 is perpendicular to the plates, it is understood that any known fixed angle may be used as long as it conforms to that used during the planning phase. Although the foregoing method is described with reference to plates, it is understood that the same method may be used for the block form of the template.

Template Alignment

FIGS. 16A-16F depict exemplary user interfaces for aligning a template to a preplanned position and orientation, according to an aspect of the invention. The following description elaborates on alignment step 1310 described above with reference to FIG. 13. Typically these images would be displayed on a display (graphical interface) associated with a computer device (e.g., computer device 301) to assist a physician in aligning the template to the planned position.

According to an aspect of the invention, various user interfaces may be used to perform alignment of the template, including a "circle alignment" (in which a pair of computer-generated circles is made to line up on a cross-hair) by monitoring the position and orientation of the template using the position sensor, and moving the circles of the graphical interface accordingly. This is a user interface that may be rapidly and easily used to align the plates either manually or with a mechanical alignment system. In addition, robotic methods may be used to align the plates.

Figure 16A:
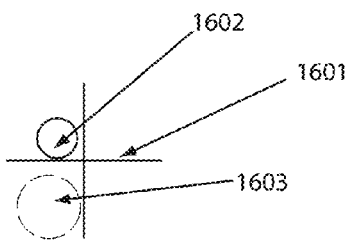
FIGS. 16A-16F depict exemplary user interfaces for aligning a template to a preplanned position and orientation, according to an aspect of the invention.
Figure 16B:
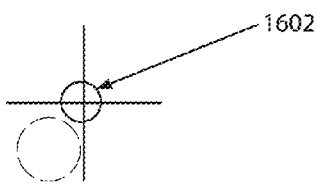

A "circle alignment" graphical aid to help position the plates is shown in FIGS. 16A-16F. In FIG. 16A, a fixed crosshair 1601 is shown along with a first circle 1602 and second circle 1603 adjacent to crosshair 1601. As the template's extension post (1506 in FIG. 15) is translated by moving the template at a fixed orientation, first circle 1602 (the "translation circle") moves in the plane of crosshair 1601 as indicated in FIG. 16B. When the position of the extension post on the skin achieves the planned pivot point, first circle 1602 will be located in the center of crosshair 1601 as shown in FIG. 16B. Because of the extension post on the plate assembly, correct positioning of translation circle 1602 is achieved by adjusting the template location in 2 directions on the skin surface (left, right, and up and down), as a third direction (moving the template closer and farther from the skin) is constrained (the post must lie on the skin surface), hence two directions on the crosshair is sufficient to determine the location of the pivot point.

Figure 16C:
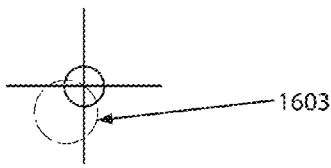
Figure 16D:
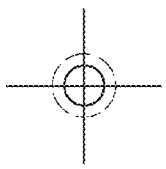
Figure 16E:
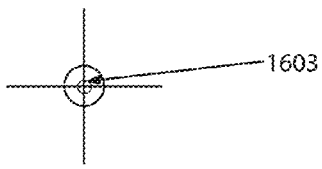

Second circle 1603 (the "orientation indication circle"), may then be moved by orienting the template by pivoting it about the pivot point on the skin surface without translating it. This action is translated by a computer program (e.g., control application 307) into a movement of second circle 1603 as shown in FIGS. 16C and 16D. In FIG. 16D, orientation in two axes and translation in three axes are aligned.

Figure 16F:
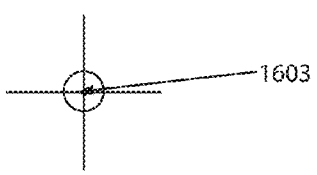

The axial rotation ("roll") of the template is the final degree of freedom, and may be achieved by maintaining the position and orientation of the template while rotating it around the axis of the extension post. To indicate this, an implementation shown in FIG. 16E and FIG. 16F uses the diameter of the second (orientation) circle 1603 to indicate the roll alignment. Second circle 1603 is made to expand or shrink so that when it is in the correct location it is rendered as a small point as shown in FIG. 16F. Other methods may be used to indicate the roll alignment such as a bar graph, color change or other graphical indication.

Once the five unconstrained parameters are aligned (the plates axial rotation, yaw, pitch, and location on the skin surface), the template is aligned and the procedure may commence. The sixth parameter, the distance from the plate to the entry point, is constrained by the extension post.

In one alternative implementation, the plates comprising the template may be manufactured during the procedure, rather than before the procedure. In such an implementation, the template plates may not be attached to a plate holder. The plate holder may be placed into a convenient position that has not been precisely planned a priori. The location and orientation of the plate holder may then be recorded using an attached tracking device and fixed in that position. If the organ of interest is registered using a method such as is known in the art (such as that, for example, disclosed in U.S. patent application Ser. No. 11/508,835 to Glossop which is hereby incorporated by reference herein in its entirety), it is possible to determine the locations of targets relative to the plate holder, and the holes in the plates may be drilled. The drilled plates may then be inserted or attached to the fixated plate holder and the procedure of inserting needles or other instruments through the holes may proceed.

In one implementation, a probe such as a tracked needle probe may be employed to verify that a plate has been created correctly, and that the outcome will be the desired one. A probe, such as that described in U.S. Pat. Nos. 6,785,571 and 7,840,251 to Glossop (each of which is hereby incorporated by reference herein in its entirety), may be inserted into the plate assembly, and the progress followed on a computer display. In addition, a tracked or untracked ultrasound may be used to verify positioning of any needle inserted into the grid.

Although the system device and method described herein are described in many places in reference to prostate therapy and biopsy, it is understood that the identical or substantially similar techniques may be applied to other organs or targets in the body with only minor modifications. For example, it may be applied to liver therapy or breast treatment by using a different support mechanism and different ultrasound transducer. It may be applied also to organs such as lungs, bones, kidney, brain, spine etc. Other minor changes such as the form of the dynamic reference device may also be required so that instead of a Foley catheter, a device such as that described in U.S. Pat. No. 7,751,868 to Glossop (which is hereby incorporated by reference herein in its entirety), may be used.

Membrane

According to an aspect of the invention, during a guided interventional procedure, a membrane may be applied to (so as to cover) a skin entry point of an instrument (e.g., a needle).

Figure 17:
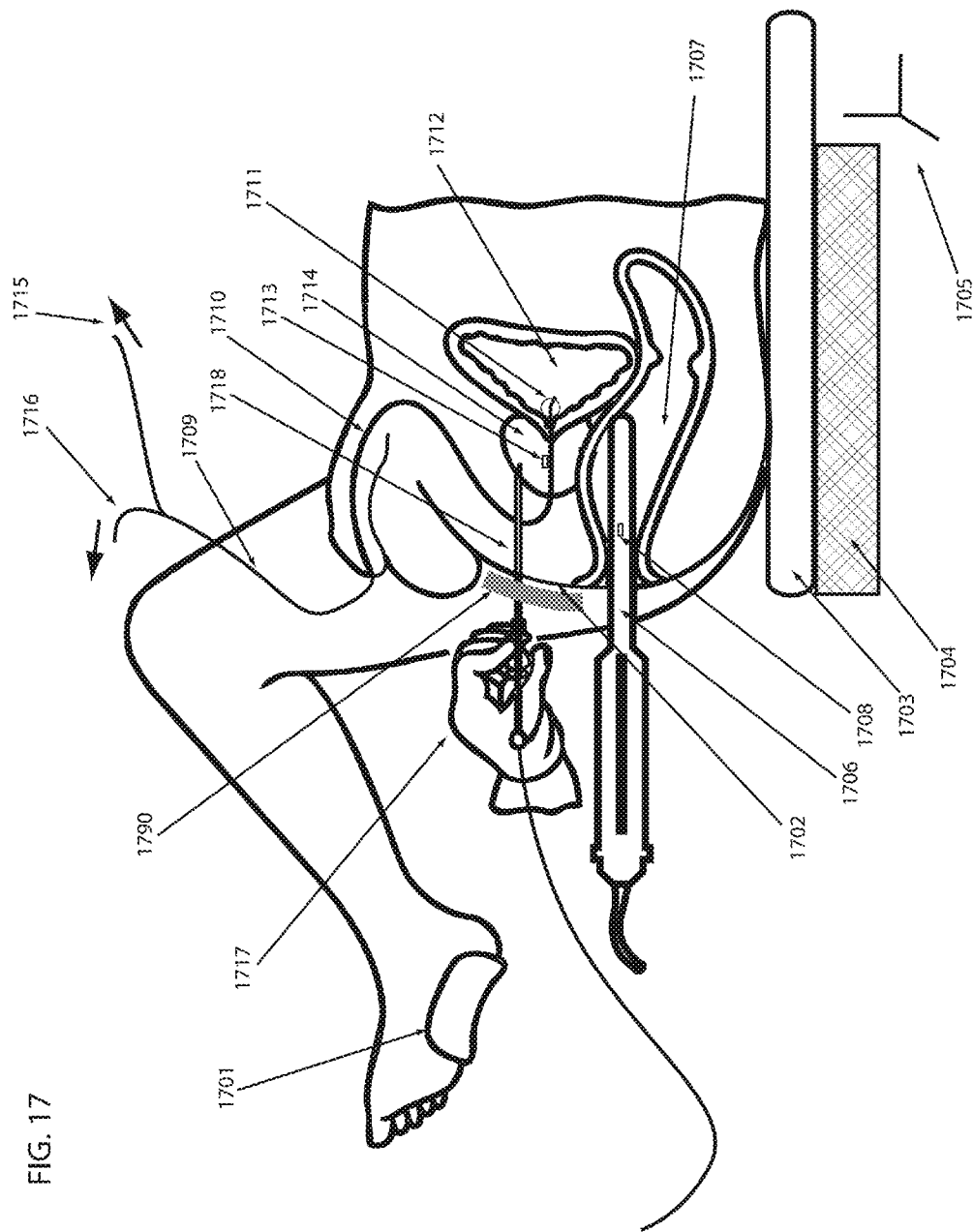
FIG. 17 is an exemplary depiction of a membrane used in a guided interventional procedure, according to an aspect of the invention.

For example, as shown in FIG. 17, membrane 1790 may cover the perineum 1702 (or other skin entry point).

In one implementation, membrane 1790 may comprise a sterile, single layer membrane composited with an adhesive film. In an alternative implementation, membrane 1790 may comprise a multilayer membrane composited with an adhesive film.

Examples of materials that may be used for the sterile, single layer membrane and the multilayer membrane may include, but are not limited to, silicone, latex rubber, thermoplastic elastomer, polyvinylchloride, or other elastomeric material composited with an adhesive film. Membrane 1790 may be releasably adhered to the perineum or other skin entry point of an instrument so as to be supportive to any instruments passing through the membrane. This will assist in maintaining the targeting of an instrument (e.g., a needle) in place such that it does not appreciably pull out or move if the patient moves, or if the instrument is subject to incidental contact, for example.

Membrane 1790 may be easily punctured by a sharp object such that a needle or other instrument may pass through the membrane easily. In this regard, the self-adhesive membrane would allow free passage of an instrument though it, but also offer support to the instrument.

In an implementation, the size and shape of membrane 1790 may be customized to provide easy placement. The membrane may also be fitted with fiducial markings in the form of points, lines, or grid lines etc. using another material or the material of the membrane that has been processed in some way so that the fiducial markings are rendered visible on one or more imaging modalities to help localize instrument placement. In an implementation, the fiducial markings may be constructed of a biocompatible and structurally stable material.

In one implementation, membrane 1790 may be used during a guided interventional procedure without a template (as shown, for example, in FIG. 17). Alternatively, a membrane may be used during a guided interventional procedure with a template. FIG. 9, for instance, depicts template 900 and membrane 990.

FIG. 17 depicts a patient lying on an operating table 1703 undergoing a procedure (in this instance, an image guided transperineal biopsy). The patient is shown in a lithotomy position with feet resting in stirrups 1701 with the patient's perineum 1702 positioned near the front of the operating table 1703. A position sensor 1704 (such as, for example, an electromagnetic field generator or optical camera array) is positioned near the patient. A coordinate system 1705 is associated with position sensor 1704. In this exemplary, and non-limiting implementation, a TRUS probe 1706 is placed in the patient's rectum 1707 to assist in visualizing the anatomy. TRUS probe 1706 may incorporate a removable or permanent position indicating element 1708 so that the location and orientation of the probe's scan plane or planes is known.

In this example, a Foley catheter 1709 may be inserted into the urethra 1710. At the distal end of catheter 1709, a balloon 1711 may be inflated to secure the catheter at the mouth of bladder 1712. On or in catheter 1709, a position indicating element 1713 may be positioned in the vicinity of the prostate gland 1714 for the purposes of dynamically referencing the prostate. Wire(s) 1715 from position indicating element 1713 may be threaded through a lumen in the catheter and connected to position sensor 1704. The lumen 1716 of catheter 1709 may be used to drain urine from the bladder.

During a guided interventional procedure, a physician (depicted here by gloved hand 1717) may use one or more instruments 1718 that may optionally include a position indicating element to assist in positioning instrument 1718 in a specific location in prostate 1714 by directly piercing the perineum 1702.

The procedure may be performed by first using TRUS probe 1706 to register the patient's prostate 1714 with the pre-operative scans and segmented images. Other registration methods may be used. Targets identified on the pre-operative images may be transferred to the live images from the ultrasound so that they appear as graphic targets on the ultrasound view. Instrument (e.g., needle) 1718 may then be directed toward each of the targets with the assistance of the position feedback obtained from the position indicating element which may also show the instrument position relative to the target as a graphic representation of an instrument tip and target.

Figure 18:
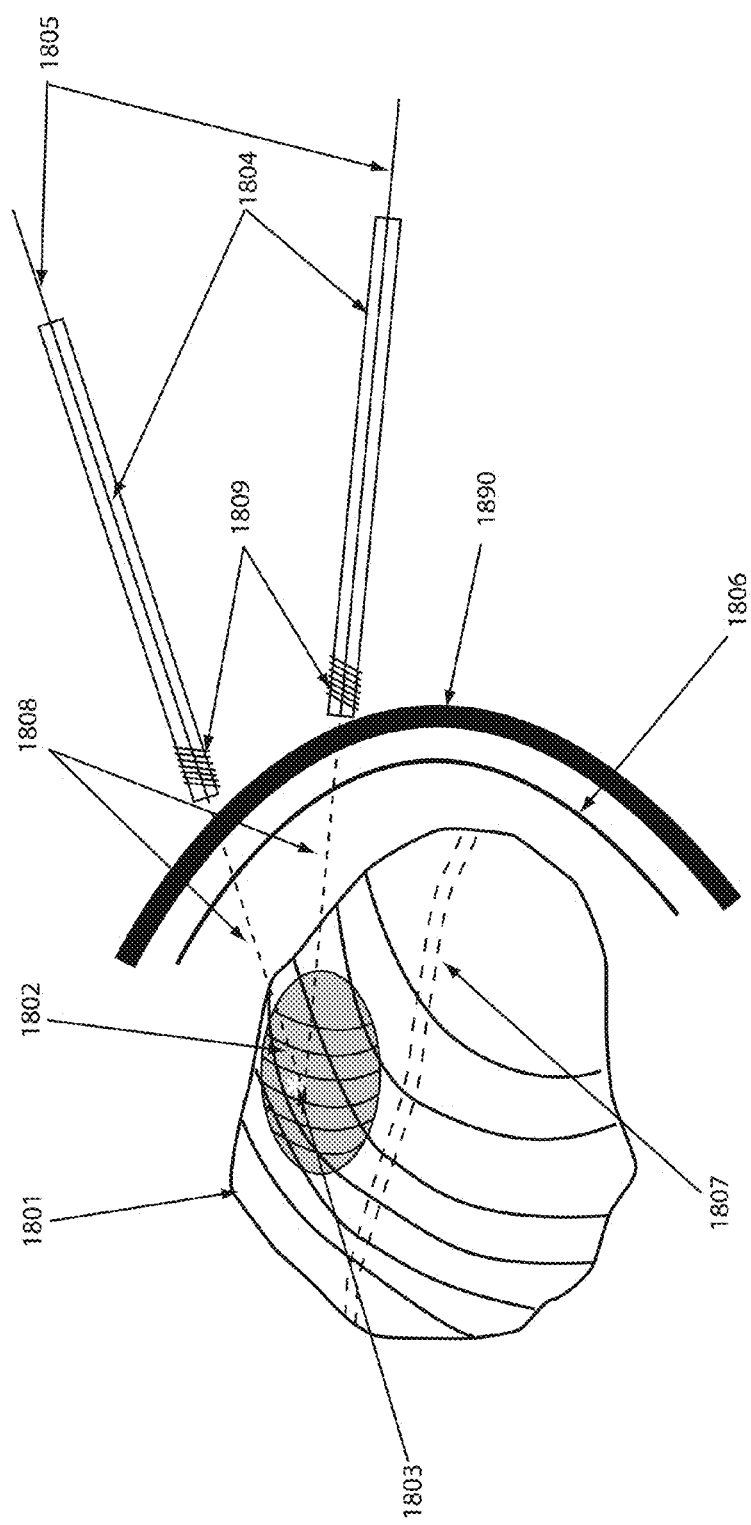
FIG. 18 is an exemplary depiction of a membrane used in a guided interventional procedure, according to an aspect of the invention.

FIG. 18 depicts a membrane 1890 (that may be affixed to a patient's skin) to aid in positioning one or more tubes during a procedure being performed on an organ 1801 (e.g., a prostate). As shown, target organ 1801 contains a suspected tumor 1802 detected on an imaging modality (e.g., such as multiparametric, MRI, or other imaging modality). Tumor 1802 may contain a target 1803 that represents the location determined by a physician during a planning phase for a biopsy, ablation, injection, device placement, or other procedure.

In an implementation, one or more hollow tubes 1804 may be positioned and angulated so that straight devices such as needles 1805 passing through the lumens of tubes 1804 and the skin surface 1806 will converge at the target or targets while avoiding critical structures such as lumen 1807 that could represent the urethra, a blood vessel, a nerve, a duct or other critical structure. In this depiction, dashed lines 1808 represent the path that devices would take if placed in tubes 1804.

In an implementation, the one or more tubes 1804 may be equipped with a position indicating element such as an LED array, or externally wrapped with a coil 1809. This enables the position indicating element to help locate the entry point and orientation of the one or more tubes 1804.

In an implementation, the tubes may be positioned by removably placing a needle containing a sensor (such as that described with reference to FIG. 2) which may be used to assist in the placement of the one or more tubes 1804 and then withdrawn. The one or more tubes 1804 may be placed using a robotic mechanism, a stereotactic mechanism, or other mechanism. In an implementation, the needles may be held in place by a support mechanism (not pictured).

Other implementations, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A template for use in a guided interventional medical procedure, the template comprising:
    a first plate and a second plate separated at a fixed distance from one another by at least one rigid spacer;
    the first plate including a first hole therethrough that defines a first trajectory entrance, and a second hole therethrough that defines a second trajectory entrance;
    the second plate including a first hole therethrough that defines a first trajectory exit, and a second hole therethrough that defines a second trajectory exit;
    wherein the first trajectory entrance of the first plate and the first trajectory exit of the second plate define a first instrument trajectory for a first medical device to be passed through the first plate and the second plate of the template;
    wherein the second trajectory entrance of the first plate and the second trajectory exit of the second plate define a second instrument trajectory for a second medical device to be passed through the first plate and the second plate of the template; and
    wherein the second instrument trajectory is not parallel to the first instrument trajectory.

2. The template of claim 1, wherein:
    the first plate includes a third hole therethrough that defines a third trajectory entrance;
    the second plate includes a third hole therethrough the defines a third trajectory exit;
    wherein the third trajectory entrance of the first plate and the third trajectory exit of the second plate define a third instrument trajectory for a third medical device to be passed through the first plate and the second plate of the template; and
    wherein the third instrument trajectory is not parallel to the first instrument trajectory or the second instrument trajectory.

3. The template of claim 1, wherein the holes defining the first trajectory entrance, the first trajectory exit, the second trajectory entrance, and the second trajectory exit comprise elliptical-shaped holes created using a three-axis Computer Numerical Control (CNC) milling machine.

4. The template of claim 1, wherein the hole defining the first trajectory entrance comprises an elliptical-shaped hole, and the hole defining the first trajectory exit comprises an elliptical-shaped hole, and the first instrument trajectory comprises an angled trajectory that is not perpendicular to the first plate and the second plate.

5. The template of claim 1, wherein the first plate and the second plate each comprise a biocompatible material.

6. The template of claim 1, wherein:
    a first marking is placed on the first plate near the hole defining the first trajectory entrance;
    a second marking is placed on the second plate near the hole defining the first trajectory exit; and
    wherein the first marking and the second marking are identical so as to convey that the first trajectory entrance and the first trajectory exit are related and collectively define the first instrument trajectory.

7. The template of claim 1, wherein the first plate and second plate are substantially planar.

8. The template of claim 1, wherein the first plate and second plate are curved.

9. The template of claim 1, wherein the first plate and second plate are positioned substantially parallel to one another.

10. The template of claim 1, wherein one or both of the first trajectory entrance and the first trajectory exit comprises a cluster of holes to enable passage of the first medical device through multiple trajectories corresponding to the first instrument trajectory through the first plate and the second plate.

11. The template of claim 1, further comprising:
    at least one fiducial feature designed to be visible under an imaging modality.

12. The template of claim 11, wherein the at least one fiducial feature comprises a hole in the first plate or the second plate, or a cut in the first plate or the second plate.

13. The template of claim 11, wherein the at least one fiducial feature comprises a hole in the first plate or the second plate filled with a contrast agent.

14. The template of claim 11, wherein the at least one fiducial feature comprises a marking placed on the first plate or the second plate.

15. The template of claim 11, wherein the at least one fiducial feature comprises a marking placed on a frame that supports the first plate and the second plate.

16. The template of claim 1, further comprising a position-indicating element that enables the position and orientation of the template to be determined in six degrees of freedom by a tracking system, the six degrees of freedom comprising an x-coordinate, y-coordinate, z-coordinate, roll, pitch, and yaw.

17. The template of claim 16, wherein the position-indicating element is integral with the first plate or the second plate.

18. The template of claim 16, wherein the position-indicating element is releasably coupled to the first plate or the second plate.

19. The template of claim 16, wherein the position-indicating element is integral with a frame that supports the first plate and the second plate.

20. The template of claim 16, wherein the position-indicating element is releasably coupled to a frame that supports the first plate and the second plate.

21. The template of claim 1, further comprising:
a support mechanism, coupled to the first plate or the second plate, that positions the template relative to an anatomical target.

22. The template of claim 1, further comprising:
a frame that supports the first plate and the second plate; and
a support mechanism, coupled to the frame, that positions the template relative to an anatomical target.

23. A method of performing a guided interventional medical procedure using a template, the method comprising:
obtaining at least one medical image of a patient's anatomy;
annotating at least one anatomical target on the at least one medical image;
generating, via a computer device, a virtual template that is positioned and oriented at a planned location relative to the at least one anatomical target on the at least one medical image;
determining, via the computer device, at least one planned trajectory that passes through the at least one anatomical target and the virtual template;
determining, via the computer device, intersection points of the at least one planned trajectory with the virtual template; and
causing a physical template to be manufactured that replicates the virtual template, the physical template comprising:
(i) a first plate and a second plate separated at a fixed distance from one another by at least one rigid spacer;
(ii) the first plate including a first hole therethrough that defines a first trajectory entrance;
(iii) the second plate including a first hole therethrough that defines a first trajectory exit; and
(iv) wherein the first trajectory entrance of the first plate and the first trajectory exit of the second plate define a first instrument trajectory for a first medical device to be passed through the first plate and the second plate of the physical template, and wherein the first trajectory entrance and the first trajectory exit correspond to the intersection points of the at least one planned trajectory with the virtual template.

24. The method of claim 23, further comprising:
registering the patient's anatomy with the obtained at least one medical image of the patient's anatomy;
aligning the physical template to the patient's anatomy in accordance with the planned location of the virtual template relative to the at least one anatomical target on the at least one medical image, such that the medical device can be placed through the physical template into the at least one anatomical target during a guided interventional medical procedure.

25. The method of claim 23, wherein the obtained at least one medical image of the patient's anatomy comprises at least one of an X-Ray image, Magnetic Resonance imaging (MRI) image, Computed Tomography (CT) image, ultrasound image, or Positron Emission Tomography (PET) image.

26. The method of claim 23, wherein annotating at least one anatomical target on the at least one medical image comprises:
annotating soft tissue.

27. The method of claim 23, wherein annotating further comprises annotating at least one critical anatomical structure on the at least one medical image, the at least one critical anatomical structure comprising a nerve, a vessel, or a bone; and
wherein determining at least one planned trajectory further comprises determining, via the computer device, at least one planned trajectory that passes through the at least one anatomical target and the virtual template, but does not pass through the at least one critical anatomical structure.

28. The method of claim 23, wherein:
the first plate includes a second hole therethrough that defines a second trajectory entrance;
the second plate includes a second hole therethrough the defines a second trajectory exit;
wherein the second trajectory entrance of the first plate and the second trajectory exit of the second plate define a second instrument trajectory for a second medical device to be passed through the first plate and the second plate of the physical template; and
wherein the second instrument trajectory is not parallel to the first instrument trajectory.

29. The method of claim 28, wherein:
the first plate includes a third hole therethrough that defines a third trajectory entrance;
the second plate includes a third hole therethrough the defines a third trajectory exit;
wherein the third trajectory entrance of the first plate and the third trajectory exit of the second plate define a third instrument trajectory for a third medical device to be passed through the first plate and the second plate of the physical template; and
wherein the third instrument trajectory is not parallel to the first instrument trajectory or the second instrument trajectory.

30. The method of claim 23, wherein:
a first marking is placed on the first plate near the hole defining the first trajectory entrance;
a second marking is placed on the second plate near the hole defining the first trajectory exit; and
wherein the first marking and the second marking are identical so as to convey that the first trajectory entrance and the first trajectory exit are related and collectively define the first instrument trajectory.

31. The method of claim 23, wherein the first plate and second plate are substantially planar.

32. The method of claim 23, wherein the first plate and second plate are curved.

33. The method of claim 23, wherein the first plate and second plate are positioned substantially parallel to one another.

34. The method of claim 23, wherein the physical template further comprises at least one fiducial feature designed to be visible under an imaging modality.

35. The method of claim 23, wherein the physical template further comprises a position-indicating element that enables the position and orientation of the physical template to be determined by a tracking system.

36. The method of claim 24, wherein registering the patient's anatomy with the obtained at least one medical image of the patient's anatomy comprises:
performing an ultrasound on the patient's anatomy and matching one or more images from the ultrasound to the obtained at least one medical image.

37. The method of claim 24, wherein the guided interventional medical procedure comprises a needle procedure.

38. The method of claim 24, wherein the guided interventional medical procedure comprises one or more of a biopsy, laser ablation procedure, microwave ablation procedure, cryoablation procedure, radiofrequency ablation procedure, high intensity focused ultrasound ablation procedure, light illumination procedure, drug delivery procedure, radiation delivery procedure, fiducial placement procedure, an application of an irreversible electroporation device, application of an electrocautery device, or application of suction.

39. The method of claim 24, wherein the medical device comprises a needle and the at least one anatomical target comprises tissue, the method further comprising:
placing the needle through the first trajectory entrance and the first trajectory exit of the physical template along the first instrument trajectory into the tissue to restrain the tissue from moving during the guided interventional medical procedure.

40. The method of claim 24, wherein the medical device is equipped with position-indicating elements rendering its position trackable.

41. The method of claim 24, wherein the medical device comprises a needle used to measure one or more of temperature, pressure, position, orientation, light intensity, radiation, a chemical or drug concentration, acoustic intensity, or electrical parameters.

42. The method of claim 23, wherein the holes defining the first trajectory entrance and the first trajectory exit comprise elliptical-shaped holes created using a three-axis Computer Numerical Control (CNC) milling machine.

43. The method of claim 28, wherein the holes defining the first trajectory entrance, the first trajectory exit, the second trajectory entrance, and the second trajectory exit comprise elliptical-shaped holes created using a three-axis Computer Numerical Control (CNC) milling machine.

44. The method of claim 23, wherein the hole defining the first trajectory entrance comprises an elliptical-shaped hole, and the hole defining the first trajectory exit comprises an elliptical-shaped hole, and the first instrument trajectory comprises an angled trajectory that is not perpendicular to the first plate and the second plate of the physical template.

45. The method of claim 23, wherein one or both of the first trajectory entrance and the first trajectory exit comprises a cluster of holes to enable passage of the first medical device through multiple trajectories corresponding to the first instrument trajectory through the first plate and the second plate of the physical template.

46. A template for use in a guided interventional medical procedure, the template comprising:
a first plate and a second plate separated at a fixed distance from one another and supported by a frame;
the first plate including a first hole therethrough that defines a first trajectory entrance, and a second hole therethrough that defines a second trajectory entrance;
the second plate including a first hole therethrough that defines a first trajectory exit, and a second hole therethrough that defines a second trajectory exit;
wherein the first trajectory entrance of the first plate and the first trajectory exit of the second plate define a first instrument trajectory for a first medical device to be passed through the first plate and the second plate of the template;
wherein the second trajectory entrance of the first plate and the second trajectory exit of the second plate define a second instrument trajectory for a second medical device to be passed through the first plate and the second plate of the template; and
wherein the second instrument trajectory is not parallel to the first instrument trajectory.

47. A method of performing a guided interventional medical procedure using a template, the method comprising:
obtaining at least one medical image of a patient's anatomy;
annotating at least one anatomical target on the at least one medical image;
generating, via a computer device, a virtual template that is positioned and oriented at a planned location relative to the at least one anatomical target on the at least one medical image;
determining, via the computer device, at least one planned trajectory that passes through the at least one anatomical target and the virtual template;
determining, via the computer device, intersection points of the at least one planned trajectory with the virtual template; and
causing a physical template to be manufactured that replicates the virtual template, the physical template comprising:
(i) a first plate and a second plate separated at a fixed distance from one another and supported by a frame;
(ii) the first plate including a first hole therethrough that defines a first trajectory entrance;
(iii) the second plate including a first hole therethrough that defines a first trajectory exit; and
(iv) wherein the first trajectory entrance of the first plate and the first trajectory exit of the second plate define a first instrument trajectory for a first medical device to be passed through the first plate and the second plate of the physical template, and wherein the first trajectory entrance and the first trajectory exit correspond to the intersection points of the at least one planned trajectory with the virtual template.

* * * * *